United States Patent

Roder et al.

Patent Number: 6,013,646
Date of Patent: Jan. 11, 2000

[54] INDOLOCARBAZOLE DERIVATIVES USEFUL FOR THE TREATMENT OF NEURODEGENERATIVE DISEASES AND CANCER

[75] Inventors: Hanno Roder, Ratingen, Germany; Timothy B. Lowinger, Nishinomiya, Japan; David R. Brittelli, Branford; Michael C. VanZandt, Guilford, both of Conn.

[73] Assignee: Bayer Corporation, Pittsburgh, Pa.

[21] Appl. No.: 09/109,131

[22] Filed: Jul. 2, 1998

[51] Int. Cl.[7] ........................ A61K 31/55; C07D 487/00; C07D 491/00
[52] U.S. Cl. ............................................ 514/219; 540/556
[58] Field of Search .............................. 540/556; 514/219

[56] References Cited

U.S. PATENT DOCUMENTS

| | | | |
|---|---|---|---|
| 4,923,986 | 5/1990 | Murakata et al. | 540/545 |
| 4,968,690 | 11/1990 | Marquez et al. | 514/303 |
| 5,189,046 | 2/1993 | Burch et al. | 514/330 |
| 5,344,926 | 9/1994 | Murakata et al. | 540/545 |
| 5,491,242 | 2/1996 | Gillig et al. | 548/455 |
| 5,516,772 | 5/1996 | Glicksman et al. | 514/211 |
| 5,594,009 | 1/1997 | Hudkins et al. | 514/338 |
| 5,599,808 | 2/1997 | Goldstein et al. | 514/211 |
| 5,607,691 | 3/1997 | Hale et al. | 424/449 |
| 5,618,809 | 4/1997 | Barrabee et al. | 514/211 |
| 5,621,101 | 4/1997 | Lewis et al. | 540/545 |
| 5,624,949 | 4/1997 | Heath, Jr. et al. | 514/410 |
| 5,648,378 | 7/1997 | Huang | 514/456 |
| 5,654,307 | 8/1997 | Bridges et al. | 514/258 |
| 5,654,427 | 8/1997 | Dionne et al. | 540/545 |
| 5,661,173 | 8/1997 | Heath, Jr. et al. | 514/414 |

FOREIGN PATENT DOCUMENTS

WO 93/03148  2/1993  WIPO .

Primary Examiner—Mukund J. Shah
Assistant Examiner—Bruck Kifle
Attorney, Agent, or Firm—Wolf, Greenfield & Sacks, P.C.

[57] ABSTRACT

Novel indolocarbazole derivatives potentially useful for the treatment of dementias characterized by tau hyperphosphorylation [Alzheimer's disease (AD), frontal lobe degeneration (FLD), argyrophilic grains disease, subacute sclerotizing panencephalitis (SSPE) as a late complication of viral infections in the CNS], and cancer.

14 Claims, 4 Drawing Sheets

INDOLOCARBAZOLE DERIVATIVES USEFUL FOR THE TREATMENT OF NEURODEGENERATIVE DISEASES AND CANCER

FIELD OF THE INVENTION

Novel indolocarbazole derivatives potentially useful for the treatment of dementias characterized by tau hyperphosphorylation [Alzheimer's disease (AD), frontal lobe degeneration (FLD), argyrophilic grains disease, subacute sclerotising panencephalitis (SSPE) as a late complication of viral infections in the CNS], and cancer.

BACKGROUND OF THE INVENTION

Several dementias, most importantly Alzheimer's disease (AD), are characterized by the formation of intracellular aggregates consisting of the microtubule-associated protein tau, termed neurofibrillary tangles (NFT). The importance of this biochemical abnormality for the clinical syndrome of dementia is illustrated by essentially three facts: (I) there is a close correlation between the state of dementia and the extent and density of NFT in various parts of the cortex [e.g., Bancher C. et al. (1993) *Neurosci. Lett.* 162, 179–182)]; (ii) individual neurons containing NFT in the cell body and/or the neurites are morphologically degenerating, i.e., lose synaptic connections and eventually die [Braak E. et al. (1994) *Acta Neuropathol.* 87, 554–567; Callahan L. M. et al., (1995) *Neurobiol. Aging* 16, 311–314]; (iii) a certain density of NFT in various otherwise unrelated dementias is always associated with dementia, without exception.

The tau protein contained in NFT is severely hyperphosphorylated [Goedert M. et al. (1995) *Neurobiol. Aging* 16, 325–334; Hasegawa M. et al. (1996) *FEBS Lett.* 384, 25–30]. This abnormal phosphorylation renders the protein incompetent to retain its original function, i.e., stabilization of the microtubule cytoskeleton, which is of fundamental importance for the integrity of a neuron [Iqbal K. et al. (1994) *FEBS Lett.* 349, 104–108; Garver T. D. et al. (1996) *J. Neurosci. Res.* 44, 12–20]. This explains the paucity of intact microtubules in AD brains. Phosphorylation alone is responsible for this effect, as dephosphorylation restores the abilities of tau.

Because of a relationship between tau phosphorylation, cytoskeletal destabilization, synaptic loss and neuronal degeneration, and ultimately dementia, it would be therapeutically desirable to have pharmaceutical means to interfere with the pathological process of tau hyperphosphorylation.

The characteristics of hyperphosphorylated tau in NFT suggest that the protein kinase ERK2 is responsible for the pathological tau modification in AD [Drewes G. et al. (1990) *EMBO J.* 11, 2131–2138; Roder H. M. et al. (1993) *Biochem. Biophys. Res. Commun.* 193, 639–647]. ERK2 may exist in an abnormally activated state in AD [Roder H. M. et al. (1995) *J. Neurochem.* 64, 2203–2212). Inhibition of ERK2 has therefore been suggested as a point of interference to prevent tau hyperphosphorylation, and ultimately to stop NFT formation in neurons.

AD-like tau hyperphosphorylation can be induced in several cellular models (including brain slices), converting tau into a phosphorylation state indistinguishable from tau phosphorylated by ERK2 in vitro. The most convincing cellular models involve PP2A inhibition [Sautiér, P. E. et al., *Neurodegeneration* 3, 53–60 (1994); Harris K. A. et al., *Ann. Neurol.* 13, 77–87 (1993)].

However, compounds which inhibit ERK2 and thereby prevent AD-like tau hyperphosphorylation in biological model systems, have previously not been disclosed. Such compounds can be expected to affect processes of neurofibrillary degeneration, tied to tau hyperphosphorylation, in a beneficial manner.

The protein kinases of the ERK family, often termed MAP-kinases, have also been implicated in a variety of important cellular regulation events outside the CNS, such as growth, differentiation and inflammation [e.g., Sale E. M. et al., *EMBO J.* 14, 674–684 (1995); Pages G. et al., *Proc. Natl. Acad. Sci. USA* 90, 8319–8323 (1993); Cowley S. et al., *Cell* 77, 841–852 (1994)]. Consequently, aberrant ERK activation has been implicated in several diseases characterized by loss of growth and differentiation control. In some tumors constitutive ERK activation is associated with cellular transformation due to dominant (activating) mutations in signal transduction proteins or viral proteins interfering with ERK inactivators [Sontag E. et al., *Cell* 75, 887–897 (1993); Leevers S. J. and Marshall C. J., *EMBO J.* 11, 569–574 (1992); Gallego G. et al., *Proc. Natl. Acad. USA* 89, 7355–7359 (1992); Gupta S. K. et al., *J. Biol. Chem.* 267, 7987–7990 (1992)].

The use of the disclosed kinase inhibitors for cancer is also indicated by their ability to inhibit cdc2 kinase. The role of cdc2 and homologous (cdks) kinases in cell cycle control is very well appreciated [Norbury C., and Nurse P., *Annu. Rev. Biochem.* 61, 441–470 (1992)]. Regulation of these enzymes is essential for both commitment to cell cycle from the resting state (START), and ordered transition through several phases of the cell cycle. The need for regulation is reflected in the existence of numerous positive and negative regulatory features of cdks, such as cyclin subunits, inhibiting (Thr) and activating (Tyr) phosphorylations, and endogenous peptide inhibitors.

Because of this central role of cdks in control of cell cycle and proliferation, they are considered as attractive drug targets for cancer therapies [e.g., Filguera de Azevedo W. et al., *Proc. Natl. Acad. Sci. USA* 93, 2735–2740 (1996)].

DESCRIPTION OF RELATED ART

Indolocarbazole derivatives structurally related to the invention compounds have been described in the literature. The majority of these compounds are derived from the natural product K252a. The production and isolation of K252a was first published by Kase, et al. [*J. of Antibiotics* 39, 1059 (1986)]. Subsequent structure elucidation of K252a, b, c and d were reported in the same year by Yasuzawa et al. [*J. of Antibiotics* 39, 1072 (1986)]. Since the original disclosure and structure elucidation, K252a has been shown to be active in a variety of enzyme and cell-based assays. In particular, these compounds have demonstrated potent protein kinase C (PKC) activity. The most common uses claimed include: cancer, EP 0 323 171 (priority date Dec. 24, 1987), EP 0 643 966 (priority date Mar. 3, 1993), U.S. Pat. No. 4,923,986 (priority date Mar. 9, 1987), U.S. Pat. No. 4,877,776 (priority date Dec. 24, 1987), WO 94 27982 (priority date May 28, 1993); neurodegenerative disorders, WO 95 07911 (priority date Sep. 16, 1993), WO 94 02488 (priority date Jul. 24, 1992), antimicrobial [Prudhomme et al., *J. Antibiotics* 47, 792 (1994)], and hypertension [Hachisu et al., *Life Sciences* 44, 1351 (1989)].

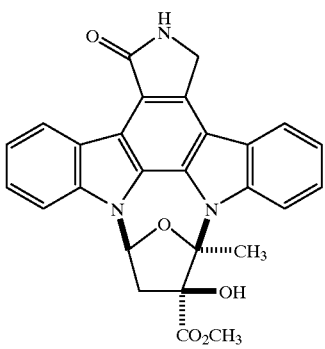

K252a

In general, prior art compounds related to the invention are derived from K252a and contain the basic core structure where a tetrahydrofuran moiety is attached to the aglycone forming two glycosidic bonds. Modifications of the K252a core structure include additional substituents on the lactam and indole portions, and modifications of the a-hydroxy ester. The tetrahydrofuran oxygen in the core structure limits the opportunities for further modification.

SUMMARY OF THE INVENTION

Incorporation of a carbon at the tetrahydrofuran oxygen position of the K252a core structure significantly alters the core structure by removing the two glycosidic bonds and replacing the electron rich disubstituted atom with an electronically more neutral tetra-substituted moiety. This change also provides additional opportunities to incorporate functional groups that may enhance properties such as potency, selectivity, stability, toxicity, bioavailability, etc. which can result in an improved biological profile and consequently, a better therapeutic agent.

Compounds containing this important modification are completely inaccessible via synthetic methods used to prepare compounds of the prior art.

According to one aspect of the invention, a composition of matter is provided having the formula of Formula I, as follows:

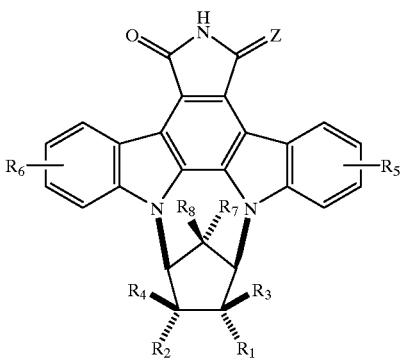

wherein Z is O or 2H (in which case the double bond is two single bonds), $R_1$ is H, OH, $CO_2R9$, CONHR9, $CH_2OR9$, or $CONR_9R_{10}$;

$R_2$ is H or OH; $R_3$ is H or OH; $R_4$ is H or OH;

$R_5$ is H, OH, $NR_9R_{10}$, $NHCOR_9$, $OCOR_9$, $OCR_9$, halide, $COOR_9$, or $CONR_9R_{10}$;

$R_6$ is H, OH, $NR_9R_{10}$, $NHCOR_9$, $OCOR_9$, $OCR_9$, halide, $COOR_9$, or $CONR_9R_{10}$;

$R_7$ is H, OH, O or halide;

R8 is H, OH, halide or nothing (when R7 is O);

R9 is an alkyl of 1–6 carbons, a cycloalkyl of 3–6 carbons or H;

R10 is an alkyl of 1–6 carbons, a cycloalkyl of 3–6 carbons or H.

In certain preferred embodiments, Z is O; R1 is OH, $CO_2R9$, CHNHR9 or $CH_2OR9$; R4 is H; R5 is H; R6 is H; and R8 is H. In other preferred embodiments, Z is O; R1 is $CO_2CH_3$ or $CONHCH_3$; R2 is H; R3 is OH; R4 is H; R5 is H; and R6 is H. The most preferred compositions of matter are:

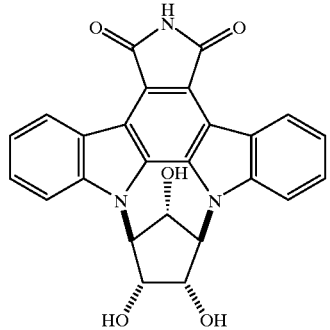

CI

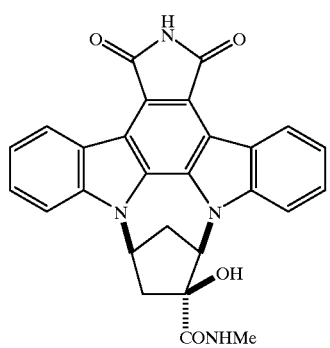

CII

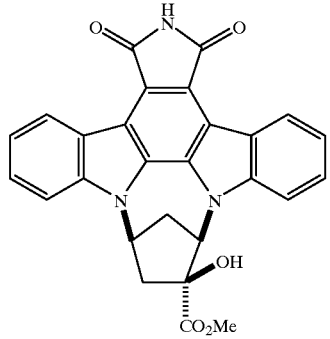

CIII

According to another aspect of the invention, pharmaceutical compositions are provided. The pharmaceutical compositions include the compositions of matter described above, together with a pharmaceutically acceptable carrier. The preferred pharmaceutical compositions are as described above. Particularly preferred pharmaceutical compositions are those formulated in an oral dosage form.

In some embodiments, the pharmaceutical composition contains the composition of matter in an amount effective for inhibiting abnormal hyperphosphorylation associated with a dementia. In other embodiments, the pharmaceutical composition contains the composition of matter in an amount effective for inhibiting a cdk kinase, such as cdc2 kinase. In still other embodiments, the pharmaceutical composition contains the composition of matter in an amount effective to inhibit cell proliferation, and in certain embodiments to inhibit cancer cell proliferation by cancer cells expressing abnormal amounts of a cdk kinase.

According to another aspect of the invention, a method is provided for inhibiting in a subject a kinase which binds a compound of Formula I. A compound of Formula I is administered to a subject in need of such treatment in an amount effective to inhibit in the subject the kinase activity. Preferred compounds are as described above. In one embodiment, the subject has a dementia and the compound is administered in an amount effective to inhibit abnormal hyperphosphorylation characteristic of the dementia. The dementia can be, among other things, Alzheimer's disease and the compound can be administered in an amount effective to inhibit phosphorylation activity of ERK2 which is characteristic of abnormal tau hyperphosphorylation in Alzheimer's disease.

According to another aspect of the invention, a method is provided for treating a subject having a cancer which expresses abnormal levels of cdk kinase activity. The method involves administering to a subject in need of such treatment a compound of Formula I in an amount effective to inhibit the cdk kinase activity. In some embodiments, the kinase is cdc2 kinase. The preferred compounds are as described above.

According to another aspect of the invention, intermediates for preparing the compounds of Formula I are provided. The intermediates are described in detail in the text below. Particularly important intermediates are those numbered 13, 19 and 24.

According to still another aspect of the invention, a method is provided which involves the use of a compound of Formula I in the preparation of a medicament. In particular embodiments, the medicament is for treating a dementia (e.g. Alzheimer's disease), a proliferative disorder (e.g. a cancer). These and other aspects of the invention are described in greater detail below.

According to another aspect of the invention, intermediates for manufacturing the above compounds are provided. These are compositions of matter comprising:

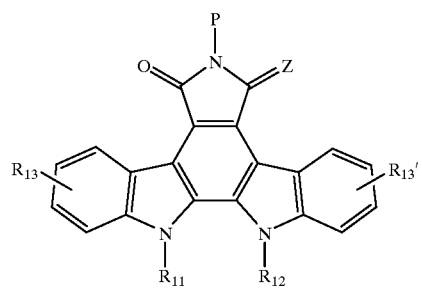

wherein, Z=O or 2H (in which case the double bond is two single bonds);

$R_{11}$, $R_{12}$=H,

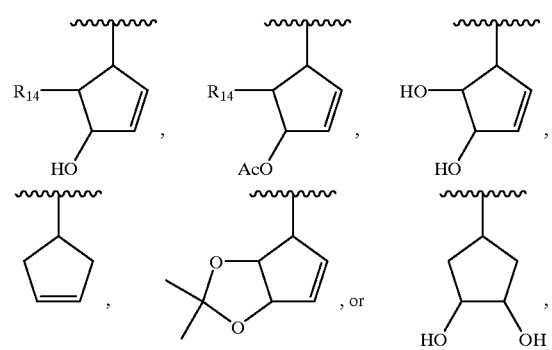

except that when $R_{11}$ is not H, then $R_{12}$ is H and when $R_{12}$ is not H, then $R_{11}$ is H;

$R_{13}$, $R_{13}'$=H or OP', and $R_{14}$ is H or OP. Preferably, Z is O and $R_{13}$ and $R_{13}'$ are H. Most preferable the composition of matter is compound 14. P is a protecting group. Preferred Ps for OP are benzyl- and t-butyl-dimethyl sylyl. Most preferably the composition of matter is compound 12, 13, 18, 19, 23 or 24.

Other compositions of matter are

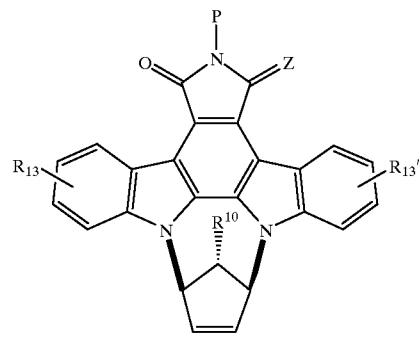

Wherein, Z=O or 2H; $R_{13}$ and $R_{13}'$=H or OP; and R14=O, H, OH or OP.

Preferably, Z is O and $R_{13}$ and $R_{13}'$ are H. Most preferably the composition of matter is compound 14.

Mixtures of the foregoing compounds including isomeric mixtures also are contemplated.

BRIEF DESCRIPTION OF THE DRAWING

FIG. 2. Western-blot comparison of tau from human SY5Y cells and from neonatal rat brain in various states of phosphorylation with PHF-tau from AD-brain.

DETAILED DESCRIPTION OF THE INVENTION

Figure 1:
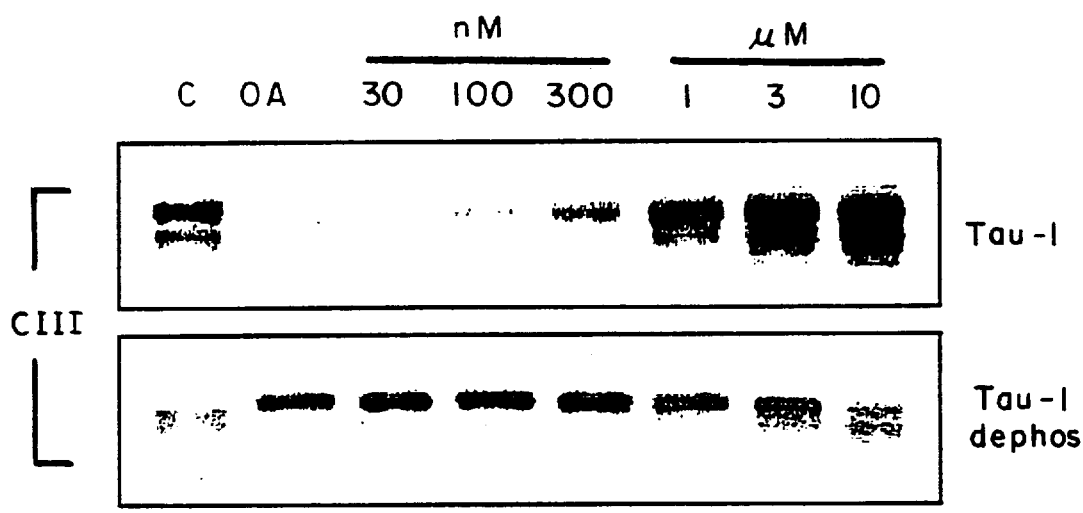
FIG. 1 is a drawing of a blot on okadaic acid stimulated cells showing that compound CIII prevent tau hyperphosphorylation caused by okadaic acid.

The present invention relates to certain novel indolocarbazole derivatives that contain a cyclopentane core structure and may be medicinally useful for the treatment of a variety of disorders, including certain cancers and neurodegenerative disorders. The compounds have ERK2 and/or cdk, and in particular, cdc2, inhibitory activity.

The compounds of the invention, including the preferred compounds have been described above. An aspect of the invention is the replacement of the oxygen molecule of the tetrahydrofuran portion of certain prior art molecules (K252a and analogs) with a carbon atom. Such a class of materials was not available prior to the present invention which also provides a synthetic procedure for preparing this class of materials. The procedure also forms an aspect of the invention. The procedure for making the class of materials is described in detail below in the Examples section.

The most preferred compounds of the invention are indicated and named below:

CI. 9,12-Methano-1H-diindolo[1,2,3-fg:3',2',1'-kl]pyrrolo [3,4-I][1,6]benzodiazocine-1,3(2H)-dione,9,10,11,12-tetrahydro-8,10,11-trihydroxy-(8α,9α,10α,11α,12α).

CII. 9,12-Methano-1H-diindolo[1,2,3-fg:3',2'0,1'-kl]pyrrolo [3,4-I][1,6]benzodiazocine-10-carboxamide, 2,3,9,10,11, 12-hexahydro-10-hydroxy-N-methyl-1,3-dioxo-(9α,10β, 12α).

CIII. 9,12-Methano-1H-diindolo[1,2,3-fg:3',2',1'-kl]pyrrolo [3,4-I][1,6]benzodiazocine-10-carboxylic acid, 2,3,9,10, 11,12-hexahydro-10-hydroxy-1,3-dioxomethyl ester, (9α, 10β,12α).

The invention also involves intermediates for manufacturing the above compounds. The intermediates are described above. Mixtures including isomeric mixtures also may result depending upon the symmetry of the starting molecule. Such mixtures are within the scope of the invention.

To prepare the full range of compounds of the invention, only the chemistry described below, together with chemistry well known to those of ordinary skill in the art is required. In particular, modifications of the core structures can be accomplished using routine chemistry such as that used to make similar modifications to k252a, as detailed in WO94/02488, WO94/27982, WO94/04541 and numerous other U.S. patents and published applications showig derivatives of k252a.

A subject as used herein means humans, primates, horses, cows, pigs, sheep, goats, dogs, cats and rodents.

The pharmaceutical preparations of the invention are administered to subjects in effective amounts. An effective amount means that amount necessary to delay the onset of, inhibit the progression of, halt altogether the onset or progression of or diagnose the particular condition being treated. In general, an effective amount for treating a dementia is that amount necessary to affect favorably abnormal hyperphosphorylation characteristic of the dementia. In one embodiment, the effective amount is that amount necessary to affect favorably abnormal tau hyperphosphorylation associated with Alzheimer's disease. In general, an effective amount for treating cancer will be that amount necessary to favorably affect mammalian cancer cell proliferation in-situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

A variety of administration routes are available. The particular mode selected will depend, of course, upon the particular condition being treated, the particular drug selected, the severity of the condition being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal, intradermal or parenteral routes. The term "parenteral" includes subcutaneous, intravenous, intramuscular, or infusion. Oral routes are preferred.

Dosage may be adjusted appropriately to achieve desired drug levels, locally or systemically. Generally, daily oral doses of active compounds will be from about 0.01 mg/kg per day to 1000 mg/kg per day. It is expected that IV doses in the range of about 1 to 1000 mg/m$^2$ per day will be effective. In the event that the response in a subject is insufficient at such doses, even higher doses (or effective higher doses by a different, more localized delivery route) may be employed to the extent that patient tolerance permits.

The compositions may conveniently be presented in unit dosage form and may be prepared by any of the methods well known in the art of pharmacy. All methods include the step of bringing the conjugates of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating solid tumors by placing the implant near or directly within the tumor, thereby affecting localized, high-doses of the compounds of the invention.

When administered, the formulations of the invention are applied in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts.

Suitable buffering agents include: acetic acid and a salt (1–2% W/V); citric acid and a salt (1–3% W/V); and phosphoric acid and a salt (0.8–2% W/V).

Suitable preservatives include benzalkonium chloride (0.003–0.03% W/V); chlorobutanol (0.3–0.9% W/V); parabens (0.01–0.25% W/V) and thimerosal (0.004–0.02% W/V).

Suitable carriers are pharmaceutically-acceptable carriers. The term pharmaceutically-acceptable carrier means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with the molecules of the present invention, and with each other, in a manner such that there is no interaction which would substantially impair the desired pharmaceutical efficacy. Carrier formulations suitable for oral, subcutaneous, intravenous, intramuscular, etc. can be found in *Remington's Pharmaceutical Sciences*, Mack Publishing Co., Easton, Pa. and in the numerous prior art patents relating to K252a and its analogs.

The compounds useful in the invention may be delivered with other therapeutic agents. In the case of cancer, the compounds would be delivered separately or in the form of anti-cancer cocktails. An anti-cancer cocktail is a mixture of any one of the compounds of this invention with another anti-cancer agent such as an anti-cancer drug, a cytokine, and/or supplementary potentiating agent(s). The use of cocktails in the treatment of cancer is routine. In this embodiment, a common administration vehicle (e.g., pill, tablet, implant, injectable solution, etc.) could contain both the compounds useful in this invention (described above) and the anti-cancer drug and/or supplementary potentiating agent.

Thus, cocktails of non-Formula I compounds and Formula I compounds are contemplated. Non-Formula I anti-neoplastic compounds include:

Antineoplastic: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin ; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin ; Cisplatin; Cladribine; Crisnatol Mesylate; Cyclophosphamide ; Cytarabine ; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride ; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198 ; Hydroxyurea; Idarubicin Hydrochloride; Ifosfamide; lmofosine; Interferon Alfa-2a; Interferon Alfa-2b ; Interferon Alfa-n1; Interferon Alfa-n3; Interferon Beta- I a; Interferon Gamma- I b; Iproplatin; Irinotecan Hydrochloride ; Lanreotide Acetate; Letrozole; Leuprolide Acetate ; Liarozole Hydrochloride; Lometrexol Sodium; Lomustine; Losoxantrone Hydrochloride; Masoprocol; Maytansine;

Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycinl, Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormiaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer Supplementary Potentiating Agents: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor.

The conjugates of the invention also are useful, in general, for treating mammalian cell proliferative disorders other than cancer, including psoriasis, actinic keratosis, etc.

General Preparative Methods

The compounds of the invention may be prepared by use of known chemical reactions and procedures. Nevertheless, the following general preparative methods are presented to aid the reader in synthesizing the inhibitors. More detailed procedures for particular examples are presented below in the experimental section.

In the general methods, the following generic descriptions apply. The group designated P represents a protecting group. It may be appreciated by one skilled in the art that a variety of different protecting groups may be used to protect a potentially reactive functional group (e.g., imide nitrogen, hydroxyl, carboxycylic acid) and that the particular choice will depend upon the reaction conditions required to prepare a given target compound. A description of such protecting groups may be found in: *Protective Groups in Organic Synthesis*, Second Edition, T. W. Green and P. G. M. Wuts, John Wiley and Sons, New York, 1991.

The group designated X represents a leaving group. It is well-known to those skilled in the art that several different functional groups such as halides, mesylates, tosylates and triflates may serve as leaving groups. It is also known that the choice of a particular leaving group typically depends on such factors as the reactivity of the nucleophile, stability of the compound and ease of synthesis. It is understood that in cases where R represents a potentially reactive functional group such as an alcohol or an amine, appropriate protection and deprotections steps may be required. It is also understood that all variable groups of these methods are as described in the generic description if they are not specifically defined below. When a variable group with a given symbol (i.e., R4) is used more than once, each of these groups may be independently varied within the range of the definition of that symbol.

General Method A The compounds of the invention where the cyclopentane ring is cis-dihydroxylated anti to the indolocarbazole moiety ($R^1, R^2$, Formula I=—OH) are conveniently prepared by method A. The first key step in the process involves the alkylation of the protected indolo[2,3-a]carbazole moiety with a suitable cyclopentane (ene) electrophile. The protected indolo[2,3-a]carbazole moiety is conveniently prepared using methods described in the literature [Lowinger, T. B. et al., *Tetrahedron Lett.* 36, 8383 (1995), P=paramethoxy benzyl]. Electrophile 11 where $R^{14}$=—H and X=OMs can be prepared from commercially available 3-acetoxy-cyclopentene-2-ol by treatment with methanesulfony chloride and triethylamine. Derivatives with $R^{14} \neq H$ can be prepared using standard methods known to those skilled in the art. Treatment of the protected indolo[2,3-a]carbazole with a base like $Cs_2CO_3$ or NaH in a polar parotic solvent like DMF followed by addition of the alkylating agent ( 11) provides the desired monoalkylated material. Conversion of 12 to alcohol 13 can be accomplished by a variety of methods well-known to those skilled in the art. One method involves a transesterification reaction where the acetate moiety is transferred to an alcoholic solvent by treatment with catalytic NaCN. Cyclization of alcohol 13 to form the 7-membered ring of 14 can be carried out using triphenylshosphine and diethyl azodicarboxylate in a reaction known as the Mitsunobo reaction. An excellent review of this chemistry is described in *Organic Reactions* 42, 335 (1992). Subsequent oxidation of 14 to diol 15 can be accomplished by an $OSO_4$ catalyzed cis-hydroxylation. The oxidation reaction is conveniently carried out using a catalytic amount of $OSO_4$ with a reoxidant such as N-methyl morpholine N-oxide (NMO) in an aqueous tetrahydrofuran (THF) or acetone solution. Similar oxidation using other metal-like Manganese and Ruthenium can also be used. The method used to remove the protecting group P from intermediate 15 will depend on the particular group used.

Deprotection of 15 where P is p-methoxybenzyl can be accomplished by treatment with trifluoroacetic acid (TFA) at elevated temperatures. Addition of a cation scavenger like anisole to the reaction mixture often results in higher yields. Those skilled in the art will appreciate that different protecting groups may be required depending on the reactivity of the various R groups.

Scheme 1 Method A

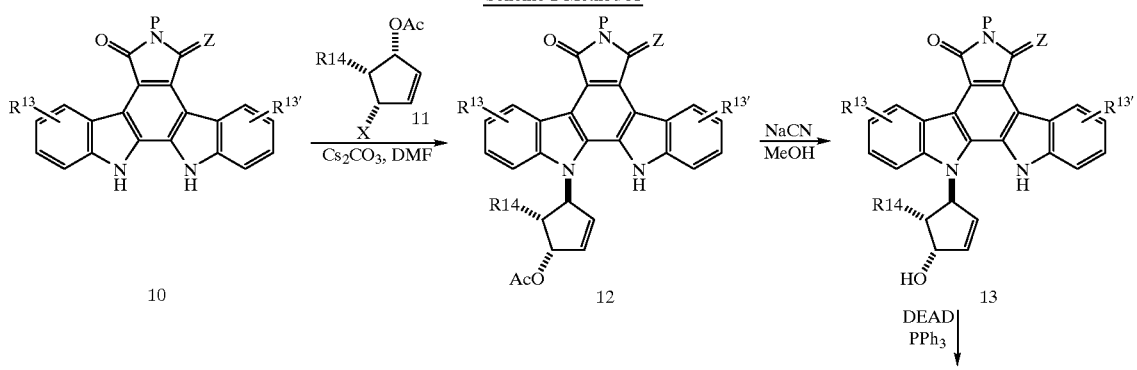

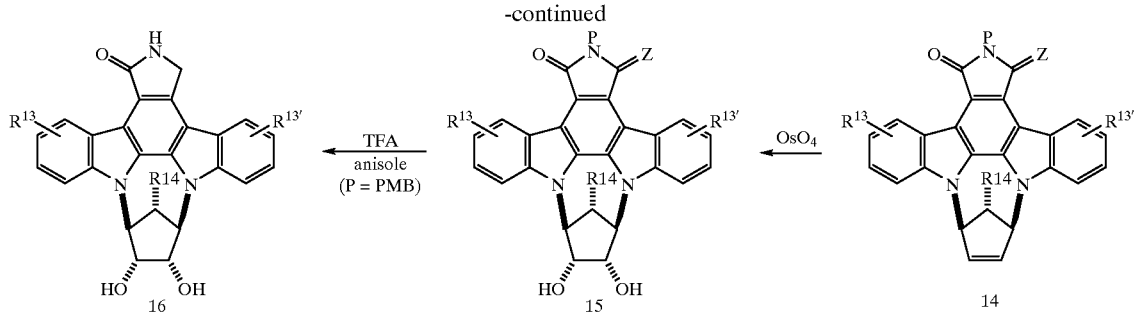

General Method B

The compounds of the invention where the cyclopentane ring is cis-dihydroxylated anti to the indolocarbazole moiety in the art will appreciate that different protecting groups may be required depending on the reactivity of the various R groups.

Scheme 2 General Method B

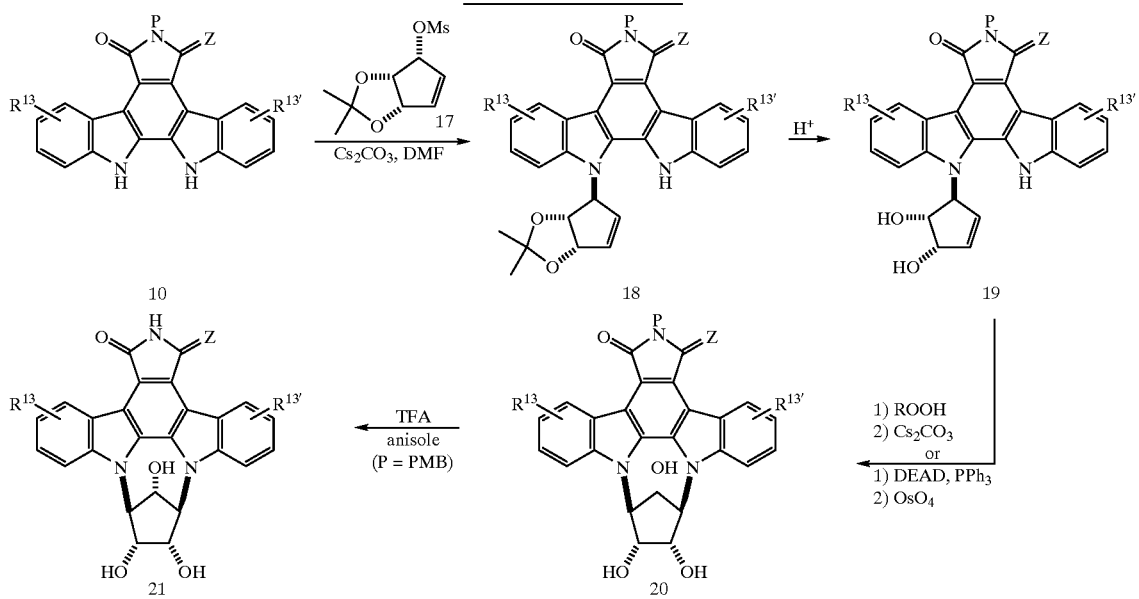

($R^1$,$R^2$, Formula I=—OH) and $R^{14}$=hydroxyl or a substituent derived from the hydroxyl group are conveniently prepared by method B. The first key step in the process involves the alkylation of the protected indolo[2,3-a]carbazole moiety with a suitable electrophile (17). The protected indolo[2,3-a]carbazole can be prepared using methods described in the literature [Lowinger T. B. et al., Tetrahedron Lett. 36, 8383 (1995), P=paramethoxy benzyl]. Alkylation of the protected indolo[2,3-a]carbazole moiety with mesylate 17 (Johnson et al. . . .) using a base like NaH or $Cs_2CO_3$ in a polar parotic solvent like DMF provides the mono-alkylated product 18. Deprotection of the acetonide moiety using standard hydrolysis conditions provide dialcohol 19. Dialcohol 19 can be converted to the cyclized product 20 by hydroxyl directed epoxidation and subsequent intramolecular alkylation, or cyclization using Mitsunobu conditions followed by cis-hydroxylation using $O_sO_4$. Deprotection of 20 where P is p-methoxybenzyl can be accomplished by treatment with trifluoroacetic acid (TFA) at elevated temperatures. Addition of a cation scavenger like anisole to the reaction mixture often results in higher yields. Those skilled

General Method C

The compounds of the invention with an α-hydroxy carboxyl moiety as illustrated in Scheme 3 are conveniently prepared using method C. The first key step in the process involves alkylation of the protected indolo[2,34-a]carbazole moiety with a wuitable cyclopentene electrophile. Protected indolo[2,3-a]carbazole moiety 10 is conveniently prepared using methods described in the literature [Lowinger T. B. et al., Tetrahedron Lett. 36, 8383 (1995) P=paramethoxy benzyl]. Electrophile 22 can be prepared from cyclopentene-3-ol by treatment with methanesulfonyl chloride and triethylamine. Cyclopenpene-3-ol can be prepared according to the procedures described in J. Org. Chem. 32, 4138 (1967). Treatment of the protected indolo[2,3-a]carbazole with a base like $Cs_2CO_3$ or NaH in a polar parotic solvent like DMF followed by addition of the alkylating agent (22) provides the desired mono-alkylated material 23. Subsequent activation of the double bond can be accomplished by an $OsO_4$ with a reoxidant such as N-methyl morpholine N-oxide (NMO) in an aqueous THF or Acetone solution. Cyclization of diol 24 using Mitsunobu conditions provides the bis alkylated adduct 25. A recent review of this Mitsunobu chemistry can be found in *Organic Reactions,* 42, 335 (1992). Oxidation of alcohol 25 to ketone 26 can be accomplished using a wide variety of reagents and reaction conditions well-known to those skilled in the art. One common method involves the use of chromium based reagents like pyrdinnium chlorochromate (PCC) in an parotic solvent such as methylenechloride. A wide variety of nucleophiles may be added to the ketone moiety in a stereoselective manner. To generate an a-hydroxy carboxyl group it is convient to add carboxylic acid anion equivalent. A general review of this methodology is described in "Unpoled Synthons", Hase T. A., Ed.; John Wiley & Sons, 1987. One example of a carboxylic acid anion equivalent is an ortho thioformyl carbanion [e.g., $LiC(SMe)_3$]. This nucleophile is conveniently prepared by treating tris (methylthio)methane with a strong base like n-BuLi. In general, the addition of the nucleophile to the ketone occurs opposite to the aglycone moiety. The thiocarboxylic acid orthoester is easily hydrolyzed by a lewis acid like boron trifluoride etherate or mercury (II) oxide. Either an ester or a carboxylic acid can be obtained from the orthoester depending on the reagents used in the hydrolysis. The methyl ester (28, Q=OMe) is conveniently obtained by treating the orthoester with mercury (II) chloride and mercury (II) oxide in aqueous methanol. The corresponding carboxylic acid (28, Q=OH) can be obtained by treatment with boron trifluoride etherate in an aqueous THF solution. Once formed, the carboxylic acid can be used as an intermediate to prepare amides (28, Q=NHMe) via a coupling reagent like carbonyldiimidizole (CDI). These procedures are well-known to those skilled in the art. The method used to remove the protecting group P from intermediate 28 will depend on the particular group used. Deprotection of 28 where P is p-methoxybenzyl (PMB) can be accomplished by treatment with trifluoroacetic acid (TFA) at elevated temperatures. Addition of a cation scavenger like anisole to the reaction mixture often results in a higher yielding reaction. Those skilled in the art will appreciate that different protecting groups may be required depending on the reactivity of the various R groups.

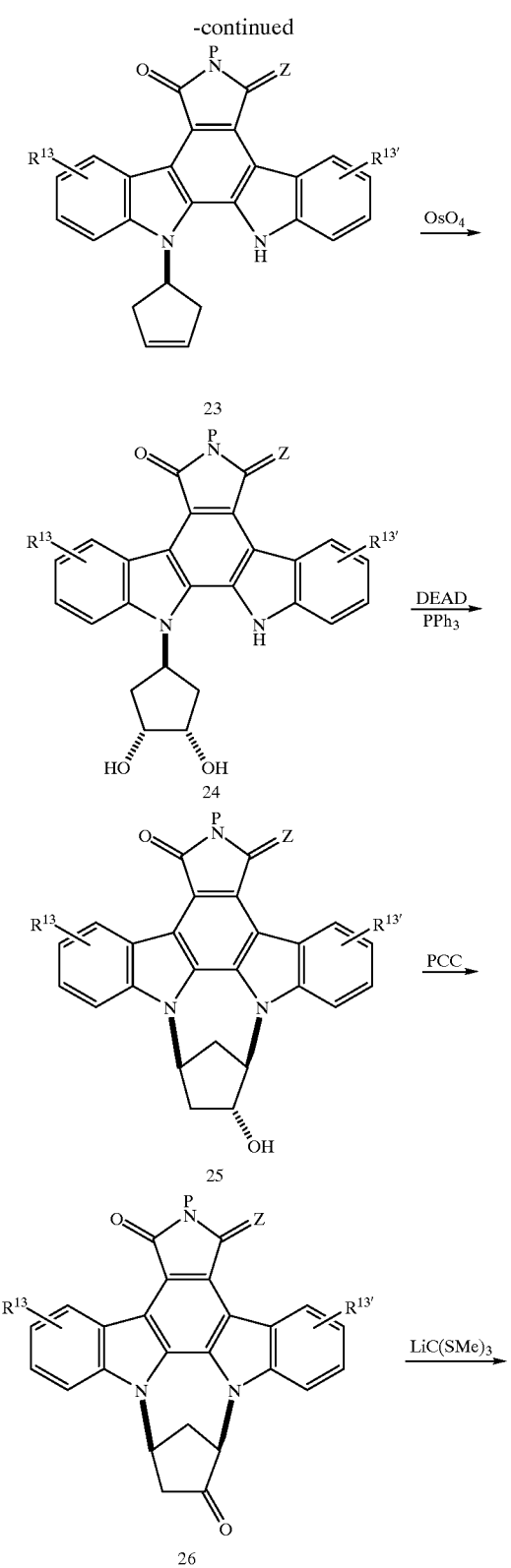

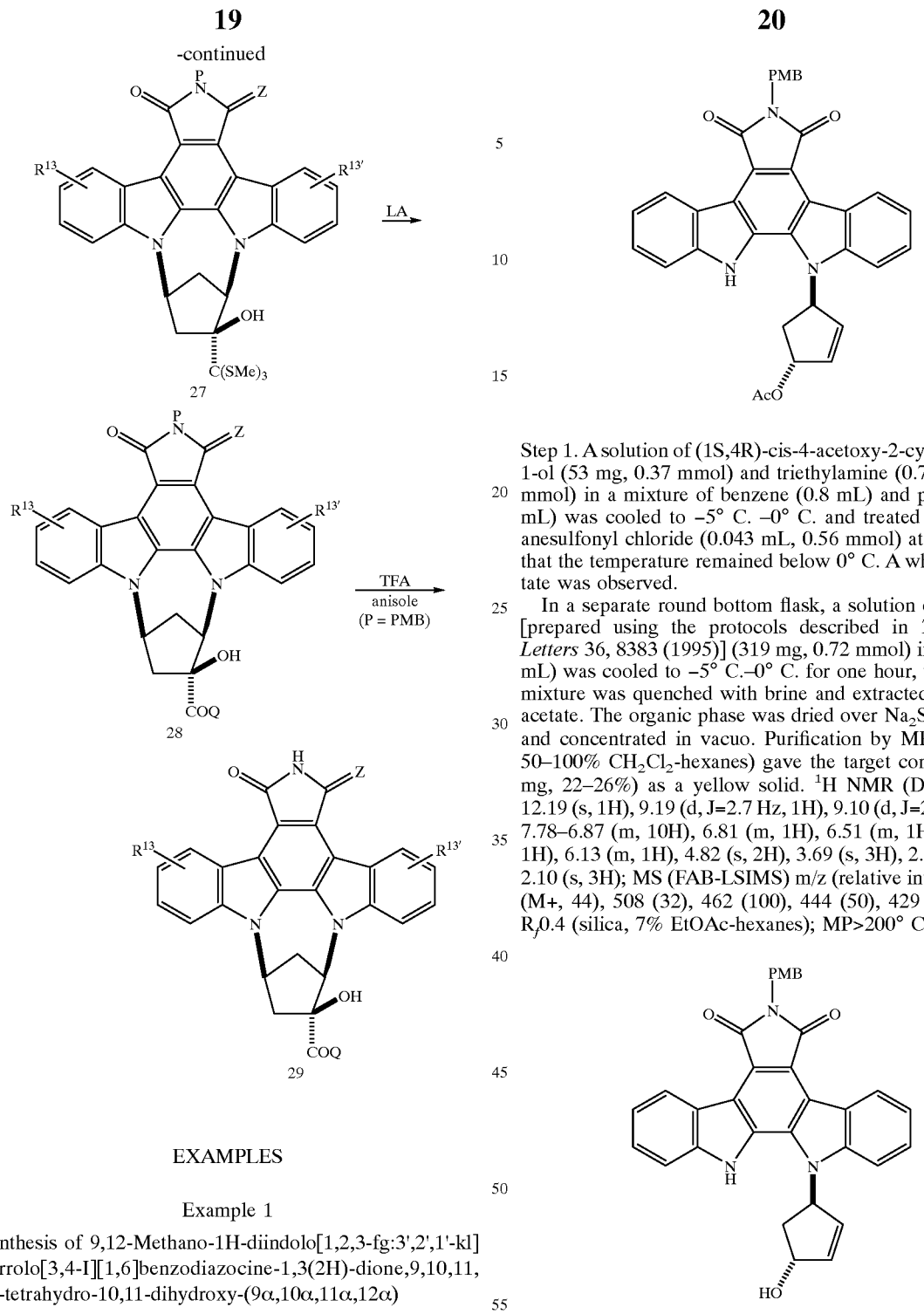

Step 1. A solution of (1S,4R)-cis-4-acetoxy-2-cyclopentene-1-ol (53 mg, 0.37 mmol) and triethylamine (0.77 mL, 0.55 mmol) in a mixture of benzene (0.8 mL) and pentane (0.8 mL) was cooled to −5° C. −0° C. and treated with methanesulfonyl chloride (0.043 mL, 0.56 mmol) at a rate such that the temperature remained below 0° C. A white precipitate was observed.

In a separate round bottom flask, a solution of aglycone [prepared using the protocols described in *Tetrahedron Letters* 36, 8383 (1995)] (319 mg, 0.72 mmol) in DMF (6.0 mL) was cooled to −5° C.–0° C. for one hour, the reaction mixture was quenched with brine and extracted with ethyl acetate. The organic phase was dried over $Na_2SO_4$, filtered and concentrated in vacuo. Purification by MPLC (silica, 50–100% $CH_2Cl_2$-hexanes) gave the target compound (55 mg, 22–26%) as a yellow solid. $^1H$ NMR (DMSO-$d_6$) δ 12.19 (s, 1H), 9.19 (d, J=2.7 Hz, 1H), 9.10 (d, J=2.7 Hz, 1H), 7.78–6.87 (m, 10H), 6.81 (m, 1H), 6.51 (m, 1H), 6.36 (m, 1H), 6.13 (m, 1H), 4.82 (s, 2H), 3.69 (s, 3H), 2.68 (m, 2H), 2.10 (s, 3H); MS (FAB-LSIMS) m/z (relative intensity) 569 (M+, 44), 508 (32), 462 (100), 444 (50), 429 (30); TLC: $R_f$ 0.4 (silica, 7% EtOAc-hexanes); MP>200° C.

EXAMPLES

Example 1

Synthesis of 9,12-Methano-1H-diindolo[1,2,3-fg:3',2',1'-kl]pyrrolo[3,4-I][1,6]benzodiazocine-1,3(2H)-dione,9,10,11,12-tetrahydro-10,11-dihydroxy-(9α,10α,11α,12α)

In order to develop more compounds having ERK2 inhibiting activity a series of synthetically modified derivatives of K252a were prepared. The preparation of four such compounds in which the preferential inhibition of PK40 over PKC/PKA was maintained by a margin of at least 2–3 orders of magnitude is described in Examples 1–4.

It is believed that these ATP analogs act as inhibitors of PK40(ERK2) by binding to the ATP binding site on PK40. PK40 seems to be particularly susceptible to inhibition by ATP analogs, resulting in similar selectivity to K252a and ATP itself.

Step 2. A solution of the acetate from step 1 (30 mg, 0.05 mmol) and sodium cyanide (10 mg, 0.2 mmol) in ethanol (2.0 mL) was heated at reflux until no starting material was observed by TLC (2 h). The mixture was concentrated in vacuo, washed in water (20 mL) and extracted with EtOAc (20 mL). The organic extract was dried over $Na_2SO_4$ and concentrated to give a yellow oil. Purification by MPLC (silica, 0–15% EtOAc-$CH_2Cl_2$) afforded the target alcohol (27 mg, 90%) as an orange powder. $^1H$ NMR (DMSO-$d_6$) δ 12.17 (s, 1H), 9.19 (d, J=2.6Hz, 1H), 9.10 (d, J=2.5 Hz, 1H), 7.78–6.87 (m, 10H), 6.79 (m, 1H), 6.28 (m, 2H), 5.25 (m, 2H), 4.83 (s, 2H), 3.68 (s, 3H), 2.54 (m, 2H); TLC (silica, 10% EtOAc-CH₂Cl₂).

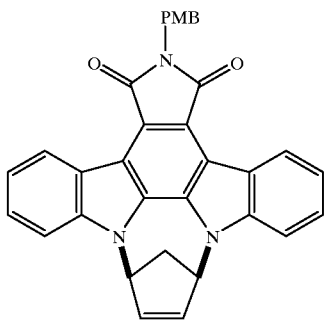

Step 3. The alcohol from step 2 was added to a solution of diethyl azodicarboxylate (65.1 mg, 0.46 mmol) and triphenylphosphine (141 mg, 0.54 mmol) in tetrahydrofuran (4.0 mL). After stirring overnight at room temperature, the reaction was quenched with brine and extracted with EtOAc. The organic phase was dried over Na₂SO₄, filtered and concentrated in vacuo. The resulting brown oil was purified by MPLC (silica, 20–30% EtOAc-hexanes) to give the cyclized product (60mg, 31%) as a yellow powder. ¹H NMR (DMSO-d₆) δ 9.07 (s, 1H), 9.04 (s, 1H), 8.02–6.87 (m, 10H), 6.41 (s 2H), 6.22 (m, 2H), 4.83 (s 2H), 3.68 (s, 3H), 3.15 (m, 1H), 2.71 (m, 1H); TLC: Rf 0.75 (silica, 50% EtOAc-hexanes).

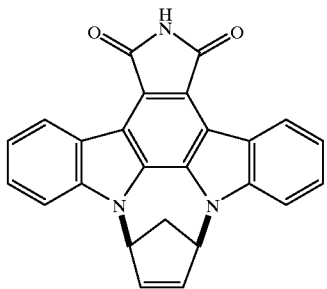

Step 4. A solution of the imide from step 3 (49.1 mg, 0.096 mmol) in anisole (0.68 mL) was stirred at room temperature for fifteen minutes and cooled to over 0° C. Over the next twenty minutes, trifluoroacetic acid (6.8 mL) was added to the solution. After allowing the orange mixture to warm to room temperature, the solution was heated to reflux overnight. After removing the solvent in vacuo, the resulting brown oil was washed with saturated. aq. NaHCO₃ (20 mL) and extracted with EtOAc (25 mL). The organic phase was dried over Na₂SO₄, filtered and concentrated in vacuo. Purification of the resulting oil via flash chromatography (silica, 0–10% EtOAc-CH₂Cl₂) gave the deprotected imide as an orange powder (34.9 mg, 93%). ¹H NMR (DMSO-d₆) δ 11.06 (s, 1H), 9.06 (s, 1H), 6.22 (d, J=2.2 Hz, 2H), 3.12 (m, 1H), 2.70 (m, 1H); MS (FAB-LSIMS) m/z (relative intensity) 390 (M+H, 60), 369 (32), 347 (62), 319 (30), 305 (18) 293 (22), 277 (100), 267 (18), 254 (28), 241 (14), 207 (14); TLC: R_f 0.50 (5% EtOAc-CH₂Cl₂). MP>230° C.

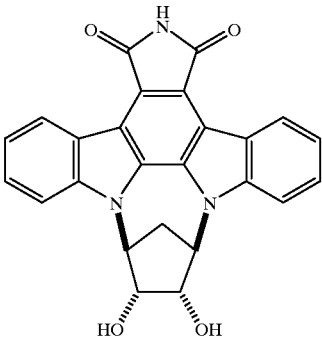

Step 5—Preparation of Example 2. A solution of the imide from step 4 (14.4 mg, 0.04 mmol) and N-methylmorpholine (0.2 mL) in tetrahydrofuran (0.4 mL) was treated with osmium tetroxide (0.1 mL, 1.0 M in THF) and stirred at room temperature for one hour (until no starting material remained by TLC, EtOAc. The reaction mixture was quenched with NaHSO₃ (1.5 mL, 2 M aqueous solution) and stirred vigorously for 1 hour. The solution was diluted with brine and extracted with EtOAc. The organic phase was dried over Na₂SO₄ and concentrated in vacuo. The resulting yellow oil was purified by HPLC (0–3% MeOH-chloroform) to afford the target diol as a red-orange powder (9.5 mg, 61%). ¹H NMR (DMSO-d₆) δ 11.05 (s, 1H), 9.05 (s, 1H), 9.02 (s, 1H), 7.85 (s, 1H), 7.65 (m, 2H), 7.39 (m, 2H), 5.51 (m, 2H), 5.39 (m, 2H), 4.06 (s, 2H), 3.27 (m, 1H); 2.40 (m 1H). MS (FAB-LSIMS) m/z (relative intensity) 424 (M+H, 34), 381 (24), 362 (12), 310 (16), 185 (42), 121 (72), 93 (100), 55 (50); TLC: R_f 0.2 (EtOAc—); MP>230° C.

Example 2

Synthesis of 9,12-Methano-1H-diindolo[1,2,3-fg:3',2',1'-kl]pyrrolo[3,4-I[1,6]benzodiazocine-10-carboxylic acid, 2,3,9,10,11,12-hexahydro-10-hydroxy-1,3-dioxomethyl ester, (9α,10β,12α).

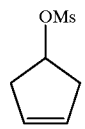

Step 1. A solution of cyclopentene-3-ol [prepared using the protocols described in J. Org. Chem. 32, 1967, 4138] (2.1 g, 25.0 mmol) and triethylamine (3.60 mL, 25.8 mmol) in CH₂Cl₂ (15.0 mL) was cooled to 0° C. and treated with methanesulfonyl chloride (1.9 mL, 24.5 mmol) at a rate such that the temperature remained below 0° C. After warming to room temperature and stirring for two hours, the reaction mixture was quenched with brine (40 mL) and extracted with CH₂Cl₂ (90 mL). The organic extract was dried over Na₂SO₄, filtered and concentrated in vacuo. Purification by MPLC (silica, 15–40% EtOAc-hexanes) gave the desired mesylate as a pale yellow liquid (3.74 g, 92%). ¹H NMR (CDCl₃) δ 5.74 (m 2H), 5.38 (m, 1H), 3.02 (s, 3 H, 2.84–2.63 (m, 4H); TLC: R_f 0.4 (40% EtOAc-hexanes).

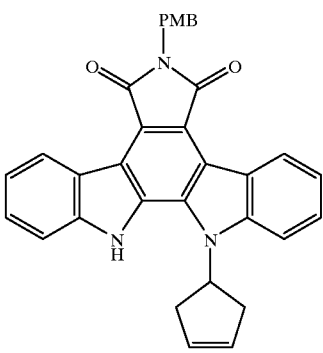

Step 2. A solution of the protected aglycone [prepared using the protocols described in *Tetrahedron Lett.* 36, 1995, 8383] (3.72 g, 8.3 mmol) in dimethylformamide (50 mL) was heated to 60–65° C. and treated with cesium carbonate (10.9 g, 33.3 mmol). The resulting dark red mixture was stirred for 30 min. Over the next four hours, the mesylate from step 1 (4.04 g, 24.9 mmol) was added in 500 mg portions and mixture stirred for two days at 65–70° C. After cooling to room temperature, the reaction mixture was quenched with brine (300 mL) and extracted with EtOAc (300 mL). The organic phase was dried over $Na_2SO_4$, filtered and concentrated in vacuo. Purification by flash chromatography (silica, 25–25% $CH_2Cl_2$-hexanes) gave the desired mono alkylated product as an orange powder (2.0 g, 47%). $^1H$ NMR (DMSO-$d_6$) δ 12.13 (s, 1H), 9.21 (d, J=2.6 Hz, 1H), 9.09 (d, J=2.7 Hz), 7.77–6.87 (m, 1H), 6.07 (s, 2H), 4.79 (s, 2H), 3.68 (s, 3H), 3.25–3.17 (m, 2H), 3.01–2.93 (m, 2H); MS (FAB-LSIMS) m/z (relative intensity) 511 (M+, 20), 419 (14), 391 (30), 378 (64) 363 (54), 255 (8); TLC: $R_f$0.5 (60% EtOAc-hexanes).

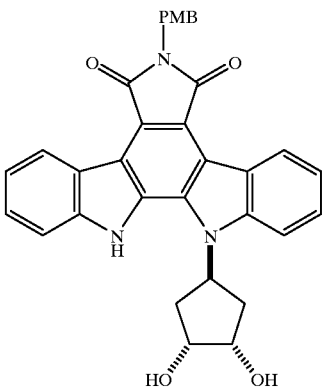

Step 3. A solution of the cyclopentene intermediate from step 2 (1.67 g, 3.26 mmol), and 4-methylmorpholine-N-oxide (60% aqueous solution, 0.55 mL, 5.31 mmol) in tetrahydrofuran (39 mL) was treated with $OsO_4$ (3.91 mL, 0.1 M in THF, 0.12 eq) and stirred overnight. After quenching mixture with aqueous 2.0 M sodium bisulfite solution and stirring for thirty minutes, the solution was extracted with EtOAc (150 mL) and washed with brine (300 mL). The organic phase was dried over $Na_2SO_4$, filtered and concentrated in vacuo. Purified by flash chromatography (silica 0–10% MeOH-EtOAc) gave the target compound as a orange-yellow solid (1.43 g, 80%). $^1H$ NMR (DMSO-$d_6$) δ 12.04 (s, 1H), 9.23 (d, J=2.7 Hz, 1H), 9.10 (d, J=2.7 Hz, 1H), 7.80–6.87(m, 10H), 6.11 (m, 1H), 4.81 (m, 4H), 4.74 (m, 2H), 3.68 (s, 3H); MS (FAB-LISMS) m/z (relative intensity) 545 (M+, 18), 438 (40), 338 (10), 255 (8); TLC: $R_f$0.2 (5% MeOH-chloroform).

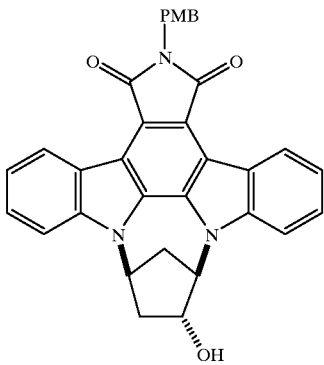

Step 4. A solution of the diol intermediate from step 3 (277 mg, 0.42 mmol) and triphenylphosphine (383 mg, 1.46 mmol) in tetrahydrofuran (26 mL) was treated with diethyl azodicarboxylate (0.16 mL, 0.98 mmol) at a rate such that the resulting orange-red color of the reaction mixture was allowed to return to its initial yellow color. After the addition was completed, the mixture was stirred for two days and subsequently heated to reflux for one day. The reaction mixture was quenched with brine (100 mL) and extracted with EtOAc (160 mL). The organic phase was dried over $Na_2SO_4$, filtered and concentrated in vacuo. Purification of the resulting oil by MPLC (silica, 0-20% EtOAc-$CH_2Cl_2$) afforded the cyclized product as an orange powder (165 mg, 75%). $^1H$ NMR (DMSO-$d_6$) δ 9.13 (d, J=2.7 Hz, 1H), 9.08 (d, J=2.7 Hz, 1H), 8.04–6.96 (m, 10H), 5.98 (m, 1H), 5.70 (m, 1H), 5.41 (m, 1H), 4.89 (s, 2H), 4.29 (m, 1 5H), 3.77 (s, 3H), 3.22 (m, 1H), 2.68 (m, 1H), 2.45 (m, 1H), 2.05 (m, 1H); MS (FAB-LSIMS) m/z (relative intensity) 527 (M+, 32), 420 (62); TLC:$R_f$0.5(30% EtOAc-$CH_2Cl_2$).

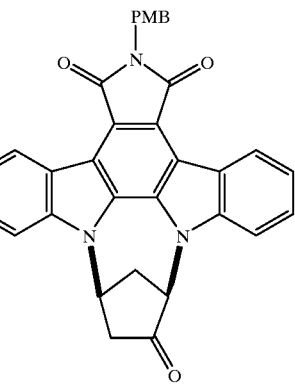

Step 5. A solution of pyridiniumn chlorochromate (89 mg, 0.41 mmol) in $CH_2Cl_2$ (2.0 mL) was treated with the alcohol from step 4 (140 mg, 0.27 mmol) as a solution in $CH_2Cl_2$ (18 mL). A second portion of pyridinium chlorochromate (40 mg) was added to the brown mixture. After stirring the mixture for 2 hours, the solution was filtered through a short pad of silica gel and concentrated in vacuo. Purification by flash chromatography (silica, 80–100% $CH_2Cl_2$-hexanes) afforded the target ketone as a yellow powder (108 mg, 77%). $^1H$ NMR (DMSO-$d_6$) δ 9.05 (d, J=2.6 Hz, 1H), 9.03 (d, J=2.4 Hz, 1H), 7.98–6.86 (m, 1H), 6.14 (m, 1H), 5.58 (m, 1H), 4.82 (s, 2H), 3.68 (s, 3H), 3.44 (m, 1H), 3.22 (m, 1H), 3.00 (M, 1H), 2.50 (m, 1H); MS (FAB-LSIMS) m/z (relative intensity) 525 (M+, 14), 418 (30), 2181 (34), 185 (100), 147 (38), 121 (66); TLC: $R_f$ 0.6 (20% EtOAc-CH$_2$Cl$_2$).

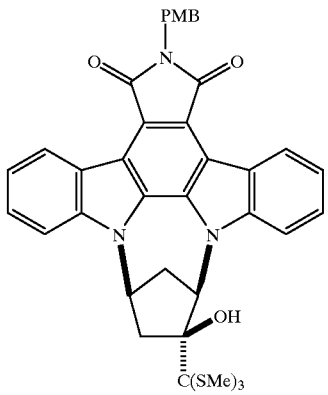

Step 6. A solution of tris(methylthio)methane (0.16 mL, 1.15 mmol) in tetrahydrofuran (3.0 mL) was cooled to −78° C. and treated with n-butyl lithium (0.59 mL, 1.6 M, 0.94 mmol). After stirring for twenty minutes, a solution of the ketone from step 5 (199 mg, 0.38 mmol) in tetrahydrofuran (6.0 mL) was added to the reaction mixture and stirred for two hours. After quenching with a saturated ammonium chloride solution (10 mL) and warming to room temperature, the reaction mixture was diluted with water (10 mL) and extracted with EtOAc (90 mL). The organic layer was separated, dried over Na$_2$SO$_4$ and concentrated in vacuo. Purification of the resulting oil by flash chromatography (silica, 20% EtOAc-hexanes) provided the addition product as a yellow solid (67 mg, 26%). $^1$H NMR (DMSO-d$_6$) δ 9.06 (m, 2H), 8.17–6.87 (m, 10H), 5.74 (m, 1H), 5.05 (s, 1H), 4.85 (s, 2H), 3.69 (s 3H), 3.01 (m, 2H), 2.17 (s, 9H); MS (FAB-LSIMS) m/z (relative intensity) 679 (M+, 12), 572 (22), 488 (24), 310 (100), 284 (86); TLC: $R_f$ 0.8 (50% EtOAc-hexanes).

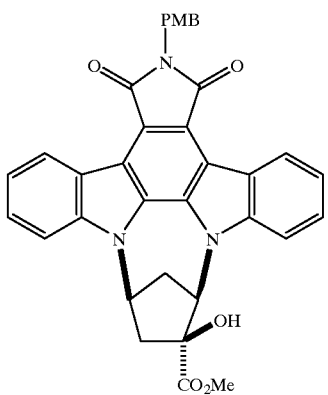

Step 7 A solution of the thiocarboxylic acid orthoester intermediate from step 6 (50 mg, 0.074 mmol) in tetrahydrofuran (5.0 mL) was treated with methanol (12.0 mL), water (1.0 mL), mercury (II) oxide (84 mg, 0.39 mmol) and mercury (II) chloride (236 mg, 0.87 mmol). The reaction mixture was heated to reflux. The solution was diluted with brine (30 mL) and extracted with CH$_2$Cl$_2$ (60 mL). The organic phase was dried over Na$_2$SO$_4$, filtered and concentrated in vacuo. Purification by flash chromatography (silica, 0–3% EtOAc-CH$_2$Cl$_2$) gave the target ester as an orange solid (18 mg, 42%). $^1$H NMR (CDCl$_3$) δ 9.25 (m, 2H), 7.60–7.40 (m, 8H), 6.88–6.85) (m, 2H), 5.61 (m, 1H), 5.40 (m, 1H), 4.93 (s, 2H), 4.03 (s, 3H), 3.77 (s, 3H), 3.21 (m, 2 H), 2.88 (m, 1H), 2.77 (m, 1H), 1.95 (m, 1H); MS (FAB-LSIMS) m/z (relative intensity) 585 (M+, 8), 478 (8), 277 (11), 185 (100); TLC: $R_f$ 0.15 (50% EtOAc-hexanes).

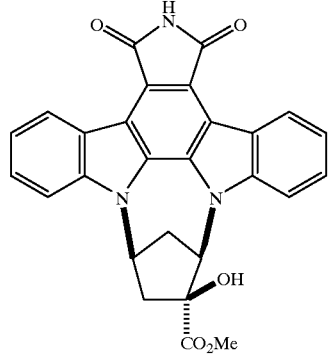

Step 8. Preparation of Example 3. A solution of the ester intermediate from step 7 (18 mg, 0.03 mmol) was dissolved in anisole (0.3 mL) over fifteen minutes and subsequently treated with trifluoroacetic acid (2.7 mL). The reaction mixture was heated to reflux for 2 hours (until no starting material remained by TLC, 5% EtOAc-CH$_2$Cl$_2$). The solution was concentrated in vacuo. Purification by flash chromatography (silica, 10–20% EtOAc-CH$_2$Cl$_2$) afforded the target imide as a yellow solid (11.0 mg, 77%). $^1$H NMR (DMSO-d$_6$) δ 11.04 (s, 1H), 9.03 (m, 2H), 7.90–7.33 (m, 6H), 5.81 (m, 1H), 5.71 (m, 1H), 5.54 (s, 1H), 3.83 (s, 3H), 3.08 (m, 2H), 2.76 (m, 1H), 1.71 (m, 1H); $^{13}$CNMR (DMSO-d$_6$) δ 175.3 (C=O), 171 (C=O imide), 170, (C=O imide,), 142.0, 140.0, 129.7, 128.4, 126.8, 126.7, 124.4, 121.3, 121.3, 121.2, 120.4, 120.2, 119.6, 119.5, 119.4, 115.3, 110.4, 109.7, 81.1 (COH), 61.7 (CHN), 55.2 (CHN), 52.07 (OCH3), 45.3, (CH2), 39.0 (CH2); MS (FAB-LSIMS) m/z (relative intensity) 466 (M+H, 14), 423 (6), 185 (28), 93 (100); TLC: $R_f$ 0.2 (5% EtOAc-CH$_2$Cl$_2$); MP>230° C.

Example 3

Synthesis of 9,12-Methano-1H-diindolol ,2,3-fg:3',2',1'-kl] pyrrolo[3,4-I][1,6]benzodiazocine-1,3,10(2H,9H)-trone, 11,12-dihydro.

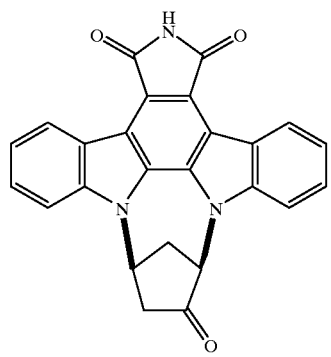

Step 1. Preparation of Example 4. A solution of the ketone for step 5 of example 2 (15 mg, 0.029 mmol) was dissolved in anisole (0.3 mL) over fifteen minutes and subsequently treated with trifluoroacetic acid (2.7 mL). The mixture was heated to reflux temperatures until no starting material was detected by TLC (10% EtOAc-CH$_2$Cl$_2$). The solution was concentrated under reduced pressure and purified by flash chromatography (silica, 0–10% EtOAc-CH$_2$Cl$_2$) to afford the target ketone (8.9 mg, 77%) as a yellow solid. $^1$H NMR (CDCl$_3$) δ 9.16 (m, 2H), 7.68–7.24 (m, 7H), 5.90 (m, 1H), 5.23 (m, 1H), 3.32 (m, 1H), 3.14–2.93 (m, 2H), 2.52 (m, 1H); MS (FAB-LSIMS) m/z (relative intensity) 405 (M+H, 12), 354 (12), 324 (18), 224 (18), 191 (52); TLC: R$_f$0.4 (10% EtOAc-CH$_2$Cl$_2$); MP>225° C.

Example 4

Synthesis of 9,12-Methano-1H-diindolo[1,2,3-fg:3',2',1'-kl] pyrrolo[3,4-I][1,6]benzodiazocine-10-carboxamide,2,3,9, 10,11,12-hexahydro-10-hydroxy-N-methyl-1,3-dioxo-(9α, 10β,12α).

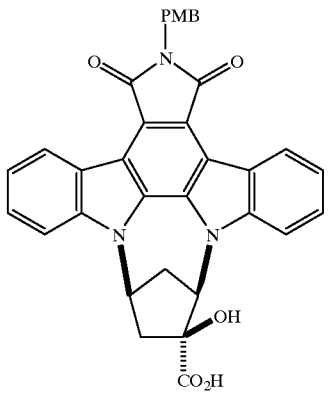

Step 1. A solution of the thiocarboxylic acid ortho ester intermediate from step 6 of example 2 (28 mg, 0.04 mmol) in 20% H$_2$O-tetrahydrofuran (1.3 mL) was treated with mercury (II) oxide (45 mg, 0.21 mmol) and boron trifluoride diethyl etherate (0.073 mL, 0.59 mmol). The reaction mixture was stirred for two hours at room temperature [until only one major spot was seen by TLC (2:3:95 acetic acid-methanol-CH$_2$Cl$_2$)], diluted with water (10 mL) and extracted with EtOAc (20 mL). The organic phase was dried over Na$_2$SO$_4$, filtered and concentrated in vacuo. Purification by flash chromatography (silica, 0–10% methanol-CH$_2$Cl$_2$) afforded the target acid as an orange solid (76%, 18.0 mg). MS(FAB-LSIMS) m/z (relative intensity) 571 (M+, 8), 464 (14), 381 (32), 330 (88), 181 (100); TLC:R$_f$0.3 (2:3:95 acetic acid-methanol-CH$_2$Cl$_2$).

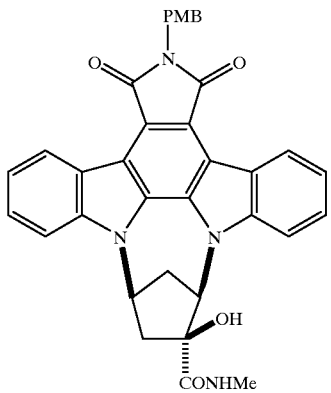

Step 2. A solution of carboxylic acid from step 1 (20 mg, 0.034 mmol) in tetrahydrofuran (2.5 mL) was cooled to 0° C. and treated with 1,1'-carbonyldiimidazole (60 mg, 0.37 mmol) and stirred for ten minutes. A solution of approximately 50% methylamine-tetrahydrofuran (2 mL) was quickly added to the reaction. After five minutes, no starting material was observed by TLC (20% EtOAc-CH$_2$Cl$_2$) and the reaction mixture was quenched with a saturated citric acid solution (3.0 mL). After warming to room temperature, the solution was diluted with brine (15 mL) and extracted with EtOAc (20 mL). The organic phase was dried over Na$_2$SO$_4$, filtered and concentrated in vacuo. Purification by flash chromatography (silica, 0–20% EtOAc-CH$_2$Cl$_2$) gave the target methyl amide (7.0 mg, 35%). MS (FAB-LSIMS) m/z (relative intensity 584 (M+, 6), 477 (8), 253 (8), 169 (84), 132 (30), 85 (100); TLC:R$_f$0.3 (20% EtOAc-CH$_2$Cl$_2$).

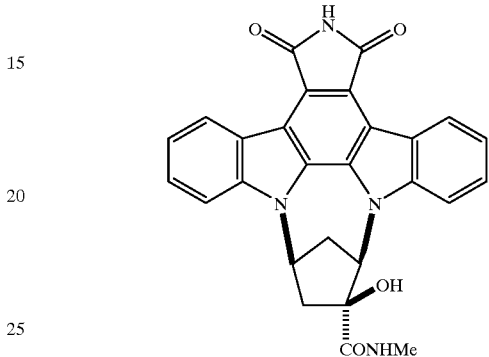

Step 3. Preparation of example 5. A solution of the protected methyl amide from step 2 (7.0 mg, 0.01 mmol) was dissolved in anisole (0.5 mL) over ten minutes and subsequently treated with trifluoroacetic acid (4.5 mL). The mixture was heated to reflux for eight hours [no starting material was observed by TLC (50% EtOAc-CH$_2$Cl$_2$)]. The mixture was concentrated in vacuo and purified by flash chromatography (silica, 10–20% EtOAc-CH$_2$Cl$_2$) to afford the methyl amide as a orange powder (3.4 mg, 61%). $^1$H NMR (DMSO-d6) δ 11.03 (s, 1HO, 9.04 (m, 2H), 7.94–7.32 (m, 7H), 5.81 (m, 1H), 5.59 (s, 1H), 5.41 (1H) 3.25–3.05 (m, 2H), 2.66 (d, J=1.5 Hz, 3H), 2.64 (m, 1H), 1.74 (m, 1H); MS (FAB-LSIMS) m/z (relative intensity) 465 (M+H, 14), 361 (82), 346 (38), 322 (100), 315 (38); TLC:R$_f$0.4 (50%EtOAc-CH$_2$Cl$_2$); MP>230° C.

Example 5

Preparation and Analysis of Kinases for Inhibitor Assays.
Preparation of Kinases:

Preparation of PKC: PKC was purified from rat brain using the method of Woodgett J. R. and Hunter T., *J. Biol. Chem* 262, 4836–4843 (1987).

Preparation of cAMP-dependent Kinase: The catalytic subunit of bovine heart PKA was obtained commercially from Sigma.

Preparation of cdc2 Kinase: Human cdc2 kinase was prepared from nocodazole-arrested HeLa cells according to Marshak D. M. er al., *J. Cell Biochem.*, 45, 391–400 (1991).

Preparation of ERK2: Recombinant human ERK2 with a N-terminal histidine (his) tag was prepared as follows: An ERK2 cDNA clone was amplified from a human frontal cortex library by PCR with primers matching the published human sequence [Gonzales F. A. et al, *FEBS Lett.* 304, 170–178 (1992)]. The histidine tag was introduced by site-directed mutagenesis. The cDNA was cloned into a pET-14b (Novagen) vector and transfected into the *E. coli* lysogen strain B121pLysS. Single colony transformants were grown in LB medium containing 35 mg/ml chloramphenicol to maintain pLysS and 50 mg/ml kanamycin to an O.D.$_{600}$ OF 0.6. The culture was then induced with 0.4 mM IPTG for 4 hours. The expressed ERK2 protein was then analyzed on a 10% SDS PAGE by both coomassie blue staining and anti-ERK Western blotting. Bacterial pellets from 0.5–1 [cultures were freeze-thawed at −78° C. and homogenized by ultra-sonication for 3 min in 15 ml $Ni^{2+}$-column buffer (20 mM Tris HCL pH 7.9, 0.5 M NaCl, 5 mM imidazole, Novagen). After centrifugation at 35,000× g for 30 min supernatants were loaded onto a 1 ml $Ni^{2+}$ charged resin (Novagen). After washing with column buffer containing 60 mM imidazole the ERK2 protein was eluted with column buffer containing 1 M imidazole. ERK2 containing fractions were identified by SDS-PAGE and dialyzed into Mono Q A-buffer (25 mM Tris HCL, pH 7.5 25 mM NaCl, 1 mM EDTA). The dialysate was loaded onto a HR5/5 Mono Q FPLC column (Pharmacia) and eluted with a 30 ml gradient from Mono Q A-buffer to the same buffer containing 250 mM NaCl (Mono Q B-buffer) at 1 ml/min collecting 30 fractions. Fractions #19–20 and #27–28 typically contained the peak amounts of two ERK2 conformers, as identified by western blotting. Only the first fraction was applied to HR 5/5 Phenylsuperose FPLC (Pharrnacia) and eluted with a 15 ml gradient from 25 mM Tris, pH 7.5, 150 mM NaCl, 1 mM EDTA, 1 mM DTT to the same buffer containing 25 mM NaCl and 60% ethylene glycol with a flow rate from 0.5 ml/min decreasing to 0.1 ml/min at the end of the gradient. Homogeneous ERK2 typically eluted after 13–14 ml.

For activation of ERK2 to the active PK40 form about 1 mg of purified histidine tagged ERK2 was mixed with 25 ml of CM-Sepharose eluate fraction prepared from bovine brain extracts according to Roder H. M. et al., *J. Neurochem.* 64, 2203–2212 (1995), adjusted to 2 mM $Mg^{2+}$/0.5 mM ATP and incubated for 2 hrs at 37° C. The mixture was dialyzed twice into 1l each of $Ni^{2+}$ column binding buffer (20 mM Tris, pH 2.9, 500 mM NaCl, 5 mM imidazole) to remove traces of DTT and loaded onto 0.3 mL $Ni^{2+}$ charged resin (Novagen) at 25 mL/hr. After washing with 10 mL column buffer followed by 4 mL column buffer containing 40 mM imidazole homogeneous activated $PK40^{erk2}$ was eluted with 4 mL column buffer containing 1 M imidazole. The product was dialyzed extensively into 10 mM HEPES, pH 7.0, 1 mM EDTA to remove imidazole and traces of $Ni^{2+}$, and finally into 10 mM HEPES, pH 7.0, 1 mM EDTA, 1 mM DTT.
Assays for Kinase Activity:

$PK40^{erk2}$ was assayed in 50μ 25 mM HEPES, pH 7.0, 1 mM $MgCl_2$, 1 mM DTT, 0.25 mM ATP, 1 mg/mL BSA using 15–30 ng of $PK40^{erk2}$ and 0.1 mg/mL myelin basic protein (Sigma) as a substrate.

PKC was assayed in 50 μl 25 mM HEPES, pH 7.0, 10 mM $MgCl_2$, 2 mM $CaCl_2$, 1 mM EDTA, 1 mM DTT, 0.25 mM ATP, 0.2 mg/mL phosphatidylserine, using 20 ng PKC and 0.08 mg/mL histone III-S as a substrate.

The catalytic subunit of PKA was assayed in 50 μl 25 mM HEPES, pH 7.0, 10 mM $MgCl_2$, 1 mM EDTA, 1 mM DTT, using 70 ng PKA and 0.1 mg/mL human recombinant tau protein as a substrate.

cdc2 kinase was assayed in 50 μl 25 mM HEPES, pH 7.0, 1 mM $Mg^{2+}$, 0.25 mM ATP (150–300 cpm/pmole), 1 mM DTT, using 0.5 ng cdc2 kinase, 5 μg human recombinant tau as substrate, and 0.1 mg/mL BSA a as carrier.
Determination of Potency of Kinase Inhibitors Enzyme, substrate and inhibitor were preincubated for 5–10 min at 4° C. in assay buffers containing a final concentration of 2% DMSO before initiating the reaction with 0.25 mM $Y^2P$-ATP. Samples were incubated for 30 min at 37° C. and reactions were terminated with 10% trichloracetic acid/2% sodium pyrophosphate (TCA/PPA), followed by filtration over a glass fiber filtermat (type A) with a cell harvester (Tomtec). The filtermats were washed twice for several hours with TCA/PPA until all background radioactivity was removed. Precipitable counts were quantitated directly on the filtermat with a microbeta scintillation counter system (Wallac-Pharmacia). Inhibitor data were subjected to curve fitting and $IC_{50}$ values were calculated from these curves using the GraphIt program.

Example 6
Determination of Potency of Inhibitors to Prevent AD-like Tau Hyperphosphoalylation in SY5Y Cell Model In vitro, and presumably also in vivo, tau is a substrate for multiple kinases. The main problem to evaluate inhibitors specifically interfering with the AD-like hyperphosphorylation of tau is to distinguish clearly between normal and abnormal phosphorylation of tau in model systems. In the cell line SY5Y comparisons can be made with tau associated with tangles from human AD brain, because of its human origin. As in fetal brains, SY5Y cells express only one of the 6 splice isoforms of tau, simplifying the survey of tau phosphorylation states.
Methods SKNSH-SY 5Y cells were plated on fibronectin-coated 6 well (30 $mm^2$) culture dishes (Biocoat®, Collaborative Biomedical Products, Inc.) and grown to confluence in 5 mL of 50% D-MEM/50% F-12 Nutrient Mixture (Ham) supplemented with 15% heat-inactivated bovine serum (JRH Bioscience), 0.1 mM non-essential amino acids solution, 2 mM glutamine and pen/strep/fungizone (GibcoBRL Life Technologies, Inc.). Cell culture medium was changed every 48 hours.

For drug testing, cells were routinely pretreated with inhibitors in 1 mL (30 $mm^2$) for 60 min at concentrations of 30 nM, 100 nM, 300 nM, 1 mM, 3 mM and 10 mM. Compound stocks were all at 10 mM in DMSO and dilutions were made in DMSO. Cells were then treated with 1 μM okadaic acid (ammonium salt; LC Laboratories, dissolved at 1 mM in DMSO) for 90 min. All experiments, including controls, contained a final concentration of between 0.5 and 1% DMSO.

Cells were detached from 30 $mm^2$ plates and suspended into 1 mL of ice-cold PBS by gentle trituration, transferred into microcentrifuge tubes and sedimented for 12 seconds at 14,000× g. The supernatant was removed and cells were lysed in 250 μl cold homogenization buffer (50 mM MES, pH 5.8, 5 mM sodium pyrophosphate, 50 mM p-nitrophenylphosphate, 1 μM okadaic acid, 2 mM Na-orthovandate, 1 mM EDTA, 1 mM EGTA, 1 mM DTT, 10^ glycerol, 10 μleupeptin, 1 μM pepstatin, 1 mg/mL aprotinin, 10 μM chymostatin, 1 mM PMSF, and 1% TRITON®×100) and vortexed briefly to aid in lysis. Cell debris was removed by centrifugation at 14,000× g for 5 minutes at 4° C. and cell supernatants were analyzed by anti-ERK2 and anti-tau Western-blotting as described below.

25 mL of total cell lysate was run on a 10% tris-glycine polyacrylamide gels (Novex, 1.5 mm×10 well) at 100 volts for 2.5 hors and Western-blotted on nitrocellulose (Novex) overnight at 23 volts or 1.5 hrs at 100 V in transfer buffer [Towbin et al. Proc. Natl. Acad. Sci. USA 76, 4350–4354 (1979)] at 4° C. Blots were analyzed for ERK2 and phosphotyrosine immunoreactivity with anti-ERK1+2 (Z033;Zymed Laboratories, Inc.; 1:5,000) and anti-phosphotyrosine (4G10; Upstate Biotechnology Inc.; 1:1, 000) mAbs. Blots were also analyzed for phosphorylation-sensitive Tau immuno-reactivity with mAb Tau-1 (Boehringer Mannheim; 1:5,000) and phosphorylation dependent mAb AT8 against FHF-tau (Biosource International; 1:200). Total Tau populations were detected by Tau-1 immunoblotting after treating blots for 16 hrs at 37° C. with 100 units/mL alkaline phosphatase (Gibco BRL) in 5 mL of 50 mM Tris-HCl (pH 8.5), 0.1 mM EDTA. All blots were developed using ECL (enhanced chemiluminescence) Western blotting protocol (Amersham Life Science) with horseradish peroxidase-linked sheep anti-mouse secondary antibody and analyzed on Kodak X-OMAT AR scientific imaging film. Films were scanned into Adobe Photoshop and imported into NIH Image 1.44, where densitometric analysis was performed. Changes in tau phosphorylation were assessed by normalizing densitometrically determined mAb Tau-1 immunoreactivities in cell extracts to Tau-1 reaction after dephosphorylation on the blot. Ratios of Tau-1 reactivity prior to and after dephosphorylation were expressed in % relative to the ratio obtained from control cells not treated with okadaic acid (100%). Proteins isolated form neonatal rat brain were used for comparison in some experiments.

Results

The potency of the compounds of the invention tested, including CII and CIII, in the in vitro kinase assay was well correlated with their inhibitory activity of tau hyperphosphorylation in the cell. Moreover, each of the compounds demonstrated a correlation between inhibition of ERK2 and tau hyperphosphorylation.

Correlation of potencies of inhibition of PK40 activity in vitro, and of OA-induced ERK2 and tau phosphorylation in SY5Y cells. ERK2 phosphorylation was quantified as the ratio of low mobility/total ERK2, densitometrically determined from ERK2 Western-blots (e.g. of FIG. 1). Tau hyperphosphorylation was expressed as densitometrically measured Tau-1 immunoreactivity normalized to total Tau-1 reactivity after unmasking of the epitope by phosphatase treatment of the blots.

Figures 2A, 2B:
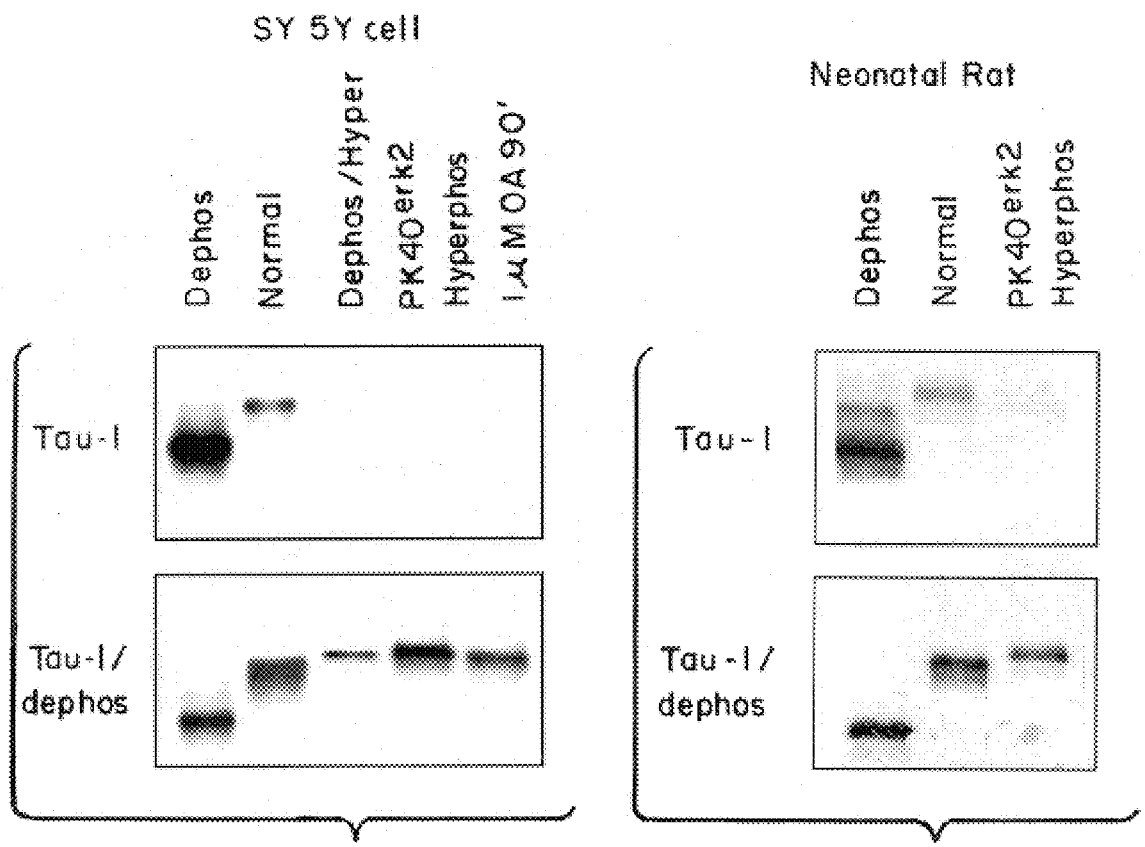
FIG. 2A shows human SY5Y cells.
FIG. 2B shows neonatal rat brain.
Figure 2C:
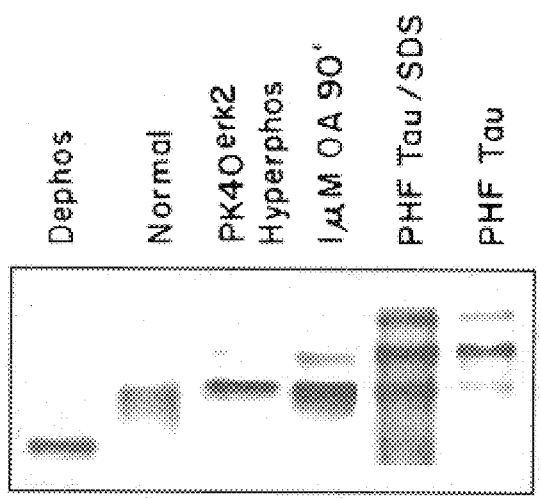
FIG. 2C shows PHF-tau from AD-brain.

In FIG. 2, tau from untreated SY5Y cells is compared to the completely hyper/dephosphorylated state (accomplished by treatment in vitro with PK40(ERK2) and phosphatase 2B, respectively), and to PHF-tau from AD brains with regard to Tau-1 immunoreactivity and electrophoretic mobility. Tau proteins were analyzed as isolated from tissue in comparison to tau exhaustively dephosphorylated with PP2B calcineurin), or hyperphosphorylated in vitro with PK40. Western-blots were stained with mAb Tau-l (FIG. 2A, B, upper panels) or AT8 (FIG. 2C, lanes 4–6). Relative gel mobilities and loading were visualized by Tau-l after complete unmasking of the epitope by phosphatase treatment on the blot (FIGS. 2A, B, lower panels; FIG. 2C, lanes 1–3). The phosphorylation of fetal tau appears to be similar to SY5Y tau. In either case hyperphosphorylation by PK40 completely abolishes residual Tau-1 reactivity and induces a small additional mobility shift. By these criteria SY5Y tau hyperphosphorylated in vitro by PK40 is indistinguishable from tau hyperphosphorylated in situ after okadaic acid induction, and from PHF-tau. Soluble fractions of PHF-tau were extracted from purified PHF by water or SDS.

FIG. 2 shows that in SY5Y cells most of the potential Tau-l reactivity is already masked by phosphorylation, and the electrophoretic mobility of tau is close to maximally retarded. By the criteria of FIG. 2, the phosphorylation state of tau in SY5Y cells does not appear to be substantially different from tau in neonatal rat brains (FIG. 2C). This probably applies to tau from adult brains as well, as newer data avoiding post-mortem artifacts in isolating tau argue against the previously held notion that the fetal phosphorylation state is higher than in the adult state.

Hyperphosphorylation with PK40(ERK2) in vitro does induce a small but detectable change in tau properties as isolated from SY5Y cells. Only in this state the electrophoretic mobility of tau matches exactly the gel mobility of the corresponding pathologically phosphorylated splice isoform extracted from tangles (FIG. 2C). In cells, the same abnormal phosphorylation state can be induced by inhibition of protein phosphatase 2A with okadaic acid.

Example 7

Methods

Figure 3:
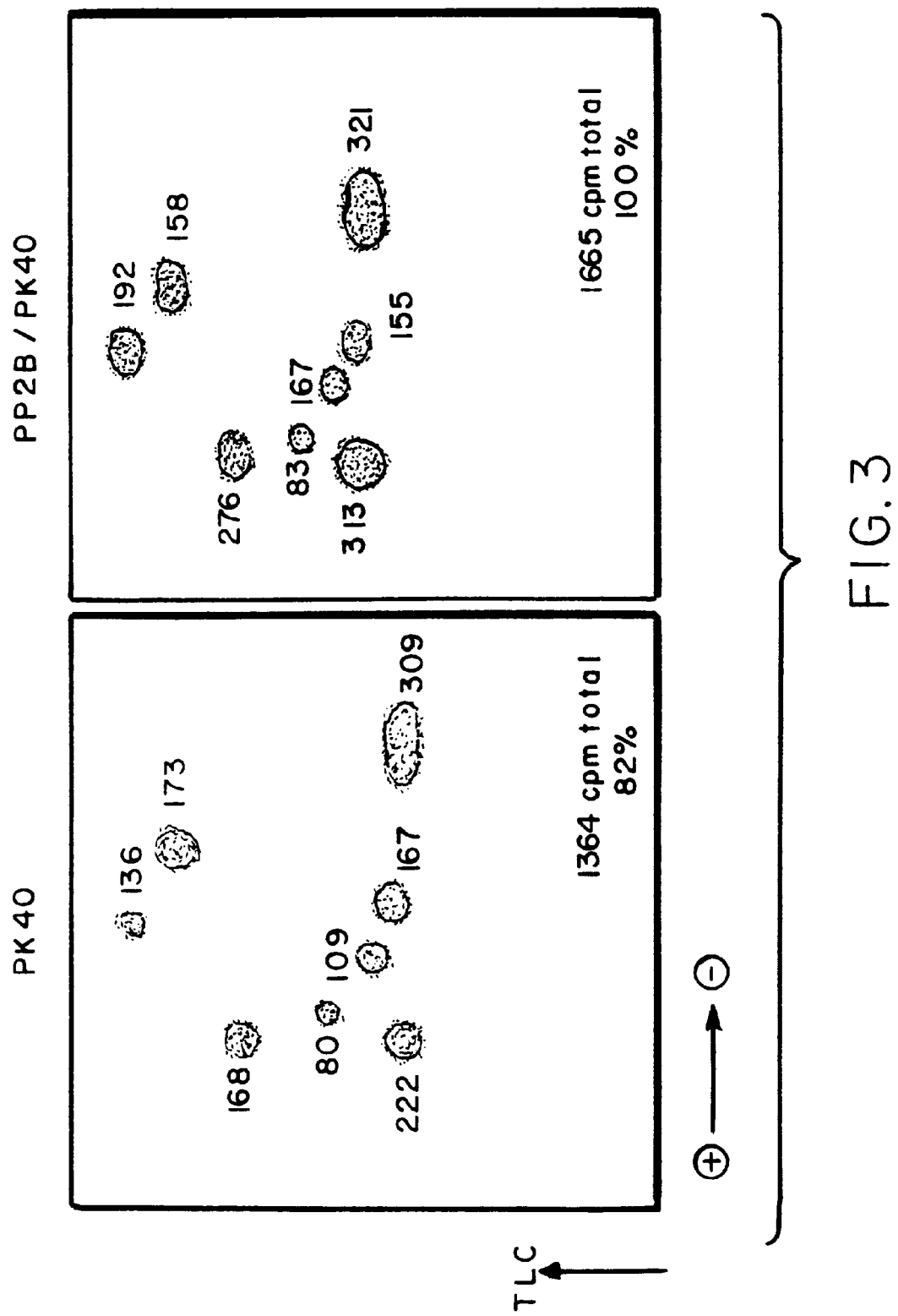
FIG. 3 is a drawing of a pair of gels showing neonatal rat tau phosphorylation in vitro by PK40 without and with prior dephosphorylation by PP2B.

Neonatal rat tau hyperphosphorylated in vitro by PK40 with or without prior dephosphorylation by PP2B. Equal amounts of purified 32P-hyperphosphorylated tau samples were digested with trypsin, and peptides were analyzed by 2D electrophoresis. The results are shown in FIG. 3. Labeling of peptides was quantified by counting (cpm displayed for each spot). Comparison of total cpm showed that dephosphorylation liberated only about ⅕th of the available ERK2 sites.

Results

In order to demonstrate that the small changes in immunochemical and gel mobility properties observed in the data presented herein is useful and a relevant model for assessing the large AD-like hyperphosphorylation effects which occur the degree of dephosphorylation/hyperphosphorylation of tau in neonatal rat cells was observed. The small change of tau associated with abnormal AD-like phosphorylation in vitro and in cells does not necessarily reflect a small change in the phosphorylation state. As shown in FIG. 3 the degree of hyperphosphorylation of tau from fetal/neonatal rat brains by PK40(ERK2) which were not pre-dephosphorylated is only about 20% lower than the degree of dephosphorylation observed when tau is dephosphorylated completely prior to hyperphosphorylation. In addition, the two-dimensional phosphopeptide maps of tau in this comparative study are qualitatively indistinguishable (FIG. 3).

Example 8

Inhibitors of PK40 Prevent Abnormal AD-like Hyperphosphorylation.

Methods

Figure 4:
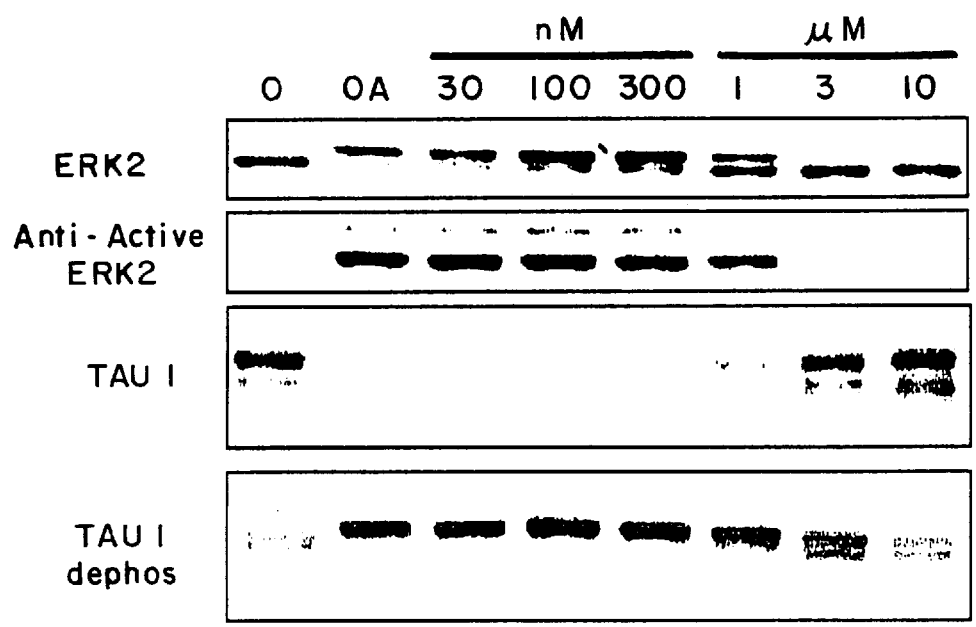
FIG. 4 is a drawing of a blot showing that a compound similar to CIII as an inhibitor of ERK2 prevents abnormal AD-like hyperphosphorylation in a SY5Y cell model system.

Compound CIII prevents ERK2 phosphorylation and tau hyperphosphorylation in a correlated fashion (FIG. 4). Compared to control cells (lane C) 1 $\mu$M okadaic acid induced ERK2 phosphorylation/activation, as shown by a small gel mobility shift of ERK2 (lane OA) and induction of reactivity with a mAb sensitive to the double phosphorylation of the regulatory Thr-Glu-Tyr motif of ERK2 (anti-active ERK2). Both effects were prevented by $\leq$1 $\mu$M compound CIII (IC50 at about 1 $\mu$M, complete at 10 $\mu$M). Highly correlated with the effect on ERK2 was the prevention of OA induced tau hyperphosphorylation, as tracked by elimination of Tau-1 reactivity and prevention of a small gel mobility shift typical of AD-like tau. Note that at 10 $\mu$M, with ERK2 activation completely arrested, the tau phosphorylation state (including the phosphoisoform pattern) remains unaltered compared to normal phosphorylation in control cells.

Prevention of tau hyperphosphorylation by the preferred compound CIII (FIG. 1). Okadaic acid at 1 $\mu$M induced the complete elimination of the Tau-1 epitope (upper panel) as in PHF-tau of AD. The shift in electrophoretic mobility corresponding to human PHF-tau was visualized by phosphatase treatment of duplicate Western-blots (lower panel) to recover the masked Tau-1 epitope. The compound CIII prevents the tau hyperphosphorylation in a dose dependent manner. At fully effective doses (>1 $\mu$M) tau remained in a phosphorylation state similar to the normal state in control cells (lane C). Tau in normal cells not treated by okadaic acid is phosphorylated to a substantial degree; this normal phosphorylation was apparently not affected by CIII. The ratio of densitometrically measured Tau-1 signal over the Tau-1 signal after dephosphorylation, a normalizing measure of the total tau population, formed the basis for quantitative analysis to determin $IC_{50}$ values.

Results

Inhibitors of PK40(ERK2), exemplified by CIII, indeed prove capable of preventing abnormal AD-like hyperphosphorylation in a SY5Y cell model system. FIG. 1 shows that increasing concentrations of CIII prevent the okadaic acid provoked hyperphosphorylation of tau. This protective effect is highly correlated with the prevention of the activating phosphorylation of ERK2 in the same cells. By binding to ERK2, CIII is able to both inhibit the activity of ERK2 as well as its activation (either via autophosphorylation or via another kinase), with both effects essentially eliminating cellular tau hyperphosphorylating activity. Moreover, the normal cellular phosphorylation state of tau is not affected by CIII in the same concentration range, demonstrating a case of cellular selectivity (not shown).

Example 9

Determination of Potency of Inhibitors to Prevent AD-like Tau Hyperphosphorylation in Rat Hippocampal Brain Slices Methods Adult male Long-Evans rats were subjected to $CO_2$ anesthesia and sacrificed by decapitation. Brains were rapidly removed (<2 min) and whole hippocampus was dissected using a blunt spatula. Hippocampi were cut into 450 mM slices using a McIlwain tissue chopper and placed into ice cold low $Ca^{2+}$ Krebs-Bicarbonate buffer (pH 7.) of the following composition in mM: NaCl, 124; KCL, 3.33; $CaCl_2$, 0.01; $KH_2PO_4$, 1.25; $MgSO_4$ 1.33; $nAhco_3$, 25.7; D-glucose, 10; HEPES, 20. The slices were separated and placed, 5–8 per tube, into 5 mL of low $Ca^{2+}$ buffer and incubated for at least 30 min at 33–34° C. with water saturated oxygenation (95% $O_2$, 5% $CO_2$). After 30 min the solution was replaced with buffer containing a physiological level of $Ca^{2+}$ (1.3 mM) and incubated for an additional 30 min.

After a total equilibration period of at least 1 hr, the slices were pretreated with vehicle or inhibitor at concentrations ranging from 30 nM to 10 $\mu$M for 1 hr, and then exposed to either vehicle or okadaic acid fora 90 min. After treatment, the buffer was removed and the slices were sonicated for 10–20 sec in 500 $\mu$l of homogenization buffer (100 mM $KH_2PO_4$, pH 6.5, 2 mM EGTA, 2 mM EDTA, 1 $\mu$M okadaic acid and the following protease inhibitors: aprotinin (10 $\mu$g/ml); leupeptin (10 $\mu$M); chymostatin (40 $\mu$M); PMSF (100 $\mu$M) and pepstatin (6 $\mu$g/ml).

Following sonication, the samples were centrifuged 16,000× g for 30 min and the supernatants were removed. After boiling of the supernatants for 5 mn at 100° C. the concentration of protein was determined by the BCA assay (Pierce) using BSA as standard and samples were normalized to equal protein concentration.

Aliquots of the heat stable supernatants were separated on 10% SDS-PAGE and Western-blotted with phosphorylation-sensitive tau mAb Tau-1 and PHF-tau mnAb AT8 as described for SY5Y studies. Blots were developed by an ECL kit (Amersham Life Science). AT8 immunoreactivity was quantitated on Kodak X0OMAT AR film using a Biorad imaging densitometer GS 670, the strongest signals not exceeding an O.D. of 12.

Results

Figure 5:
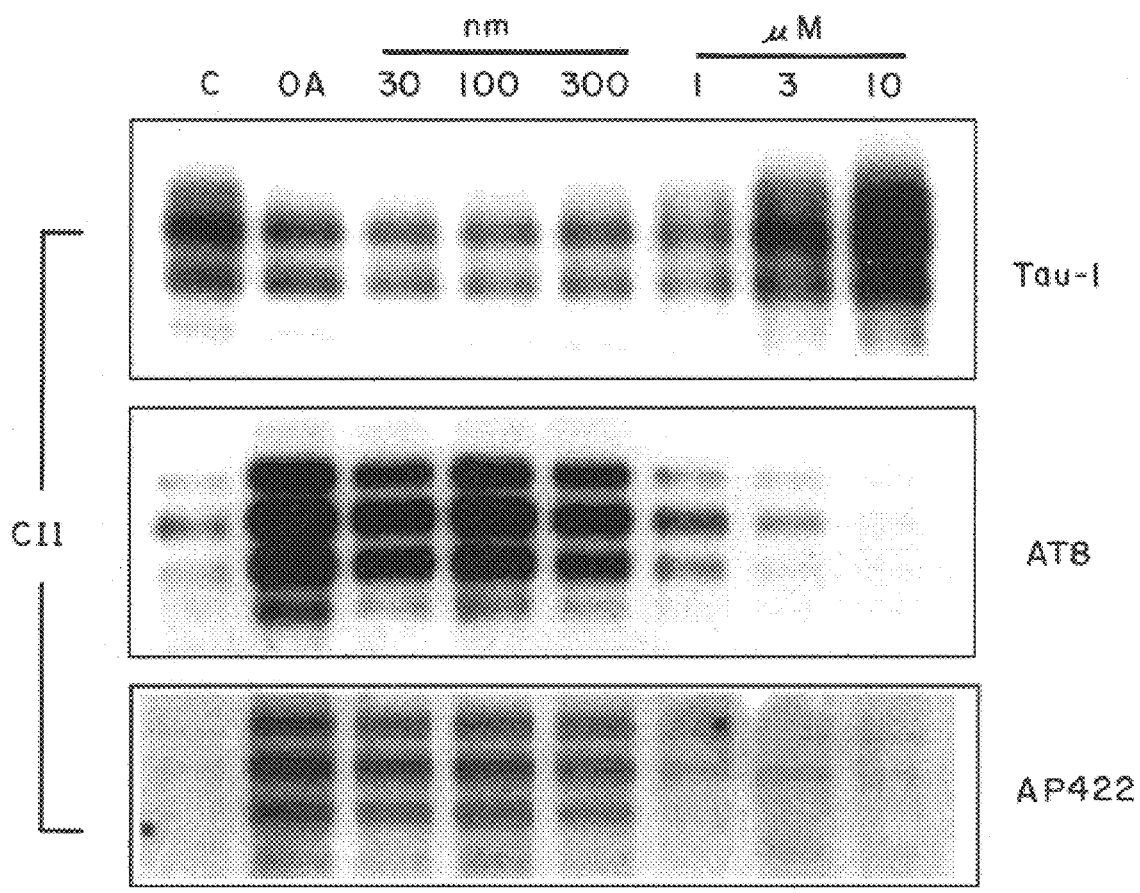
FIG. 5. Prevention of AD-like tau hyperphosphorylation in adult rat hippocampal brain slices. In an experimental paradigm similar to SY5Y cells tau hyperphosphorylation is prevented by CII at similar doses as in SY5Y cells. Note that the results with AP422, currently the most specific criterion for AD-like tau hyperphosphorylation, are identical to those with the commonly used mAb AT8, indicating that ERK2 alone is responsible for all okadaic acid induced changes in tau phosphorylation because AT8 but not AP422 reactivity can be induced by kinases other than ERK2.

Freshly isolated hippocampal brain slices from adult rats were used for similar experiments under conditions more relevant to the brain (FIG. 5). Again, okadaic acid induced AD-like tau hyperphosphorylation, while CII prevented it with the same IC50 as in SY5Y cells (0.1 $\mu$M).

Okadaic acid induced reactivity with the novel phosphorylation dependent mAb AP422. This response was inhibited at the same dose as the response with the more conventional mAb AT8 (FIG. 5), indicating a single tau hyperphosphorylating activity. In vitro reactivity of tau with this mAb can only be induced by ERK2, but not other candidate tau kinases (e.g. cdk, GSK3), providing an independent criterion that ERK2 is the relevant drug target.

The intensity of AP422 reactivity induced by PK40 (ERK2) in vitro matches that of isolated PHF-tau from AD-brain (not shown). In contrast, even with the most conservative precautions to avoid post-mortem dephosphorylation in rat brains, AP422 reactivity is completely absent in normal adult tau. This suggests that tau hyperphosphorylation in AD is qualitatively abnormal, and does not involve enhanced activity of normal kinases, but rather the pathological activation of ERK2 as an abnormal tau kinase.

Prevention of AD-like tau hyperphosphorylation in adult rat hippocampal brain slices. In an experimental paradigm similar to SY5Y cells tau hyperphosphorylation is prevented by derivative CII at similar doses as in SY5Y cells.

Note that the results with AP422, currently the most specific criterion for AD-like tau hyperphosphorylation, are identical to those with the commonly used mnAb AT8, indicating that ERK2 alone is responsible for all okadaic acid induced changes in tau phosphorylation.

TABLE 1

Properties of Preferred Compounds as Inhibitors of ERK2 (PK40), Activation of ERK2, cdc2, and Tau Hyperphosphorylation in Biological Models of PHF-tau formation ($IC_{50}$ values in $\mu$M)

|  | CII | CIII |
| --- | --- | --- |
| PK40 (ERK2) | 0.044 | >>30 |
| cdc2 | 0.044 | 3.3 |
| PKA | 0.65[a] | >100 |
| PKC | 0.65[a] | >100 |
| Inhibition in SY5Y cells[b] of ERK2 activation | 0.57 | 5.7 |
| tau hyperphos. | 0.58 | 3.6 |
| Inhibition of tau hyperphos. in brain slices[b] | 0.18 | 0.9 |

[a] = partial inhibition only
[b] = means of triplicate determinations
[c] = concomitant inhibition of normal tau phosphorylation

We claim:

1. A composition of matter comprising: (Formula I)

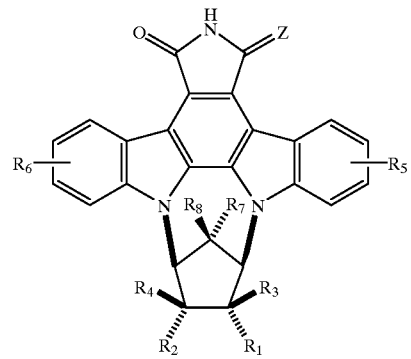

wherein Z is O or 2H, $R_1$ is H, OH, $CO_2R_9$, $CONHR_9$, $CH_2OR_9$, or $CONR_9R_{10}$;

$R_2$ is H or OH; $R_3$ is H or OH; $R_4$ is H or OH;

$R_5$ is H, OH, $NR_9R_{10}$, $NHCOR_9$, $OCOR_9$, $OCR_9$, halide, $COOR_9$, or $CONR_9R_{10}$;

$R_6$ is H, OH, $NR_9R_{10}$, $NHCOR_9$, $OCOR_9$, $OCR_9$, halide, $COOR_9$, or $CONR_9R_{10}$;

$R_7$ is H, OH, O or halide;

$R_8$ is H, OH or halide; or $R_7$ and $R_8$ together form =O;

$R_9$ is an alkyl of 1–6 carbons, a cycloalkyl of 3–6 carbons or H;

$R_{10}$ is an alkyl of 1–6 carbons, a cycloalkyl of 3–6 carbons or H.

2. The composition of matter of claim 1, wherein Z is O; $R_1$ is OH, $CO_2R_9$, $CONHR_9$, $CH_2OR_9$; $R_4$ is H; $R_5$ is H; $R_6$ is H; and $R_8$ is H.

3. The composition of matter of claim 1, wherein Z is O; $R_1$ is $CO_2CH_3$ or $CONHCH_3$; $R_2$ is H; $R_3$ is OH; $R_4$ is H; $R_5$ is H; and $R_6$ is H.

4. The composition of matter of claim 1, wherein the composition of matter is selected from the group consisting of:

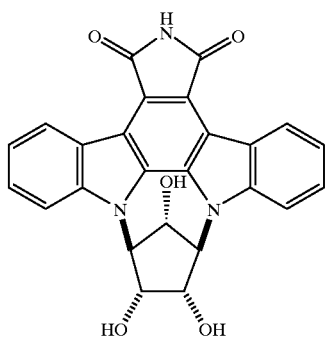

CI

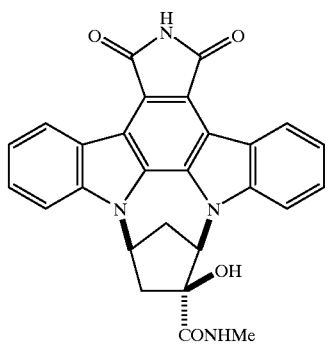

CII

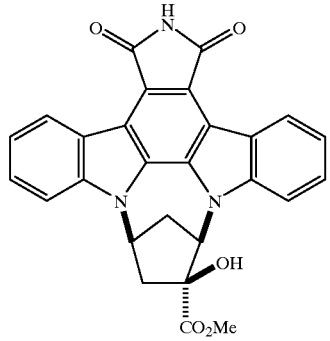

CIII

5. A pharmaceutical composition comprising:
the composition of matter of claim 1, and
the pharmaceutically-acceptable carrier.

6. A pharmaceutical composition comprising:
the composition of matter of claim 2, and
a pharmaceutically-acceptable carrier.

7. A pharmaceutical composition comprising:
the composition of matter of claim 3, and
a pharmaceutically-acceptable carrier.

8. A pharmaceutical composition comprising:
the composition of matter of claim 4, and
a pharmaceutically-acceptable carrier.

9. The pharmaceutical composition of claim 5 in an oral dosage form.

10. The pharmaceutical composition of claim 6 in an oral dosage form.

11. The pharmaceutical composition of claim 7 in an oral dosage form.

12. The pharmaceutical composition of claim 8 in an oral dosage form.

13. A composition of matter comprising

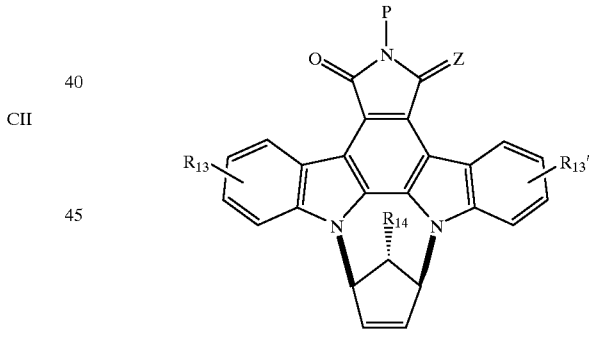

wherein, Z=O or 2H; $R_{13}$, $R_{13}'$=H or OP; and $R_{14}$=O, H, OH or OP. Preferably, Z is O and $R_{13}$ and $R_{13}'$ are H.

14. The composition of claim 13 wherein Z=O and $R_{13}$ and $R_{13}'$=H.

* * * * *